United States Patent
Miles et al.

(10) Patent No.: US 11,096,972 B2
(45) Date of Patent: *Aug. 24, 2021

(54) SENECA VALLEY VIRUS (SVV) CELLULAR RECEPTOR TARGETED ONCOTHERAPY

(71) Applicant: Memorial Sloan-Kettering Cancer Center, New York, NY (US)

(72) Inventors: Linde Miles, New York, NY (US); John Poirier, New York, NY (US); Charles Rudin, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 16/747,433

(22) Filed: Jan. 20, 2020

(65) Prior Publication Data

US 2020/0222480 A1 Jul. 16, 2020

Related U.S. Application Data

(63) Continuation of application No. 15/780,898, filed as application No. PCT/US2016/064679 on Dec. 2, 2016, now Pat. No. 10,537,599.

(60) Provisional application No. 62/262,242, filed on Dec. 2, 2015.

(51) Int. Cl.
| | |
|---|---|
| A61K 35/768 | (2015.01) |
| C12Q 1/6886 | (2018.01) |
| A61P 35/00 | (2006.01) |
| G01N 33/574 | (2006.01) |
| A61K 45/06 | (2006.01) |

(52) U.S. Cl.
CPC ............ *A61K 35/768* (2013.01); *A61K 45/06* (2013.01); *A61P 35/00* (2018.01); *C12Q 1/6886* (2013.01); *G01N 33/57484* (2013.01); *C12N 2770/32033* (2013.01); *C12Q 2600/106* (2013.01); *C12Q 2600/158* (2013.01); *G01N 2800/52* (2013.01)

(58) Field of Classification Search
CPC .. A61K 35/768; A61K 38/21; A61K 39/0011; A61K 38/212; A61K 38/217; C12N 2710/24132; C12N 2710/10332; C12N 2710/10032; C12N 5/0693; C12Q 1/6886; C12Q 2600/158; C12Q 2600/106; C12Q 2600/112; A61P 35/00
See application file for complete search history.

(56) References Cited

U.S. PATENT DOCUMENTS

| | | |
|---|---|---|
| 2006/0159659 A1 | 7/2006 | Hallenbeck et al. |
| 2009/0304728 A1 | 12/2009 | Concetti et al. |
| 2010/0183633 A1 | 7/2010 | Davis et al. |

FOREIGN PATENT DOCUMENTS

| | | |
|---|---|---|
| WO | 2008112891 A2 | 9/2009 |
| WO | 2014089124 | 6/2014 |

OTHER PUBLICATIONS

McDermott et al. Drugs Today (Barc) Jan. 2015;51(1), pp. 7-20.*
Gunturi et al. Expert Opin Investig Drugs Actions published by Feb. 2015;24(2), pp. 253-260.*
Lynch et al Jo. Clin. Oncol. 2012, vol. 30(17), pp. 2046-2054.*
International Written Opinion for International Application No. PCT/US2016/064679 dated Feb. 7, 2017 [Cited in Parent U.S. Pat. No. 10,537,599 issued on Jan. 21, 2020].
International Search Report for International Application No. PCT/US2016/064679 dated Feb. 7, 2017 [Cited in Parent U.S. Pat. No. 10,537,599 issued on Jan. 21, 2020].
Poirier, John T. et al., "Characterization of a full-length infectious cDNA clone and a GFP reporter derivative of the oncolytic picornavirus SVV-001," J. Gen. Viral., vol. 93, pp. 2606-2613, 2012 [Cited in Parent U.S. Pat. No. 10,537,599 issued on Jan. 21, 2020].
Shalem, Ophir et al., "Genome-scale CRISPR-Cas9 knockout screening in human cells," Science, vol. 343, pp. 84-87, 2014 [Cited in Parent U.S. Pat. No. 10,537,599 issued on Jan. 21, 2020].
Reddy, Seshidhar P., et al., "Seneca Valley virus, a systemically deliverable oncolytic picornavirus, and the treatment of neuroendocrine cancers," J. Natl.Cancer Inst., vol. 99, pp. 1623-1633, 2007 [Cited in Parent U.S. Pat. No. 10,537,599 issued on Jan. 21, 2020].
Sanjana N.E. et al., "Improved vectors and genome-wide libraries for CRISPR screening," Nature Methods, vol. 11, pp. 783-784, 2014 [Cited in Parent U.S. Pat. No. 10,537,599 issued on Jan. 21, 2020].
Hansson, Mattias D. et al., "Sirijovski, N. PCR-mediated deletion of plasmid DNA," Anal Biochem, vol. 375, pp. 373-375, 2008 [Cited in Parent U.S. Pat. No. 10,537,599 issued on Jan. 21, 2020].
Barretina, Jordi., et al., "The Cancer Cell Line Encyclopedia enables predictive modelling of anticancer drug sensitivity," Nature, vol. 483, pp. 603-607, 2012 [Cited in Parent U.S. Pat. No. 10,537,599 issued on Jan. 21, 2020].
Neale, Geoffrey et al., "Molecular characterization of the pediatric preclinical testing panel," Clinical cancer Research: An Official Journal of the American Association for Cancer Research, vol. 14, pp. 4572-4583, 2008 [Cited in Parent U.S. Pat. No. 10,537,599 issued on Jan. 21, 2020].
Isella, Claudio et al., "Stromal contribution to the colorectal cancer transcriptome," Nature Genetics, vol. 47, pp. 312-319, 2015 [Cited in Parent U.S. Pat. No. 10,537,599 issued on Jan. 21, 2020].
Zilliox, Michael J. et al., "A gene expression bar code for microarray data," Nature Methods, vol. 4, pp. 911-913, 2007 [Cited in Parent U.S. Pat. No. 10,537,599 issued on Jan. 21, 2020].

(Continued)

*Primary Examiner* — Bao Q Li

(74) *Attorney, Agent, or Firm* — Hunton Andrews Kurth LLP

(57) ABSTRACT

A method for selecting cancer patient for treatment with Seneca Valley Virus (SVV) by determining expression of ANTXR1 in a cancerous tissue in a cancer patient; and designating the cancer patient as a candidate for treatment with SVV if normal levels or elevated levels of ANTXR1 expression is detected in the cancerous tissue. Also a method for treating a cancer patient with SVV is disclosed.

15 Claims, 5 Drawing Sheets

(56) References Cited

OTHER PUBLICATIONS

Wu, Di et al., "Camera: A competitive gene set test accounting for inter-gene correlation," Nucleic Acids Res. vol. 40, p. e133, 2012 [Cited in Parent U.S. Pat. No. 10,537,599 issued on Jan. 21, 2020].
Hanzelmann, Sonja et al., "GSVA: Gene set variation analysis for microarray and RNA-seq data," BMC Bioinformatics, vol. 14, No. 7, pp. 1-15, 2013 [Cited in Parent U.S. Pat. No. 10,537,599 issued on Jan. 21, 2020].
Tang, Guano et al., "EMAN2: An extensible image processing suite for electron microscopy," Journal of Structural Biology, vol. 157, pp. 38-46, 2007 [Cited in Parent U.S. Pat. No. 10,537,599 issued on Jan. 21, 2020].
Scheres, S.H., "RELION: Implementation of a Bayesian approach to cryo-EM structure determination," Journal of Structural Biology, vol. 180, pp. 519-530, 2012 [Cited in Parent U.S. Pat. No. 10,537,599 issued on Jan. 21, 2020].
Venkataraman, Sangita, et al., "Structure of Seneca Valley Virus-001: An oncolytic picornavirus representing a new genus," Structure, vol. 16, pp. 1555-1561, 2008 [Cited in Parent U.S. Pat. No. 10,537,599 issued on Jan. 21, 2020].
Pettersen, Eric F. et al., "UCSF Chimera—A visualization system for exploratory research and analysis," Journal of Computational Chemistry, vol. 25, pp. 1605-1612, 2004 [Cited in Parent U.S. Appl. No. 10,537,599 issued on Jan. 21, 2020].
Cong, Le et al., "Multiplex genome engineering using CRISPR/Cas systems," Science, vol. 339, pp. 819-823, 2013 [Cited in Parent U.S. Pat. No. 10,537,599 issued on Jan. 21, 2020].
Mali, Prashant, et al., "RNA-guided human genome engineering via Cas9," Science, vol. 339, pp. 823-826, 2013 [Cited in Parent U.S. Pat. No. 10,537,599 issued on Jan. 21, 2020].
Jinek, Martin., et al. "A programmable dual-RNA-guided DNA endonuclease in adaptive bacterial immunity," Science, vol. 337, pp. 816-821, 2012 [Cited in Parent U.S. Pat. No. 10,537,599 issued on Jan. 21, 2020].
Carette, J.E., et al., "Ebola virus entry requires the cholesterol transporter Niemann-Pick C1," Nature, vol. 477, pp. 340-343, 2011 [Cited in Parent U.S. Pat. No. 10,537,599 issued on Jan. 21, 2020].
Bradley, Kenneth A. et al., "Identification of the cellular receptor for anthrax toxin," Nature, vol. 414, pp. 225-229, 2001 [Cited in Parent U.S. Pat. No. 10,537,599 issued on Jan. 21, 2020].
Poirier, J.T. et al., "Selective tropism of Seneca Valley virus for variant subtype small cell lung cancer," J. Natl Cancer Inst., vol. 105, pp. 1059-1065, 2013 [Cited in Parent U.S. Pat. No. 10,537,599 issued on Jan. 21, 2020].

Milacic, Marija et al.,"Annotating cancer variants and anti-cancer therapeutics in reactome," Cancers, vol. 4, pp. 1180-1211, 2012 [Cited in Parent U.S. Pat. No. 10,537,599 issued on Jan. 21, 2020].
Croft, David et al., "The Reactome pathway Knowledgebase," Nucleic Acids Res., vol. 42, pp. 472-477, 2014 [Cited in Parent U.S. Pat. No. 10,537,599 issued on Jan. 21, 2020].
Morton, Christopher L. et al., "Initial testing of the replication competent Seneca Valley virus (NTX-010) by the pediatric preclinical testing program," Pediatric Blood Cancer, vol. 55, pp. 295-303, 2010 [Cited in Parent U.S. Pat. No. 10,537,599 issued on Jan. 21, 2020].
Nguyen, T.L., et al., "Chemical targeting of the innate antiviral response by histone deacetylase inhibitors renders refractory cancers sensitive to viral oncolysis," Proc. Natl. Acad. Sci. USA, vol. 105, pp. 14981-14986, 2008 [Cited in Parent U.S. Pat. No. 10,537,599 issued on Jan. 21, 2020].
Tuthill, T.J. et al., "Picornaviruses," Current topics in microbiology and Immunology, vol. 343, pp. 43-89, 2010 [Cited in Parent U.S. Pat. No. 10,537,599 issued on Jan. 21, 2020].
Strauss, Mike et al., "Nectin-like interactions between poliovirus and its receptor trigger conformational changes associated with cell entry," Journal of Virology, vol. 89, pp. 4143-4157, 2015 [Cited in Parent U.S. Pat. No. 10,537,599 issued on Jan. 21, 2020].
Kolatkar, Prasanna et al., "Structural studies of two Rhinovirus serotypes Complexed with fragments of their cellular Receptor," The EMBO Journal, vol. 18, pp. 6249-6259, 1999 [Cited in Parent U.S. Pat. No. 10,537,599 issued on Jan. 21, 2020].
Organtini, Lindsey J. et al., "Kinetic and structural analysis of coxsackievirus B3 receptor interactions and formation of the A-particie," Journal of Virology, vol. 88, pp. 5755-5765, 2014 [Cited in Parent U.S. Pat. No. 10,537,599 issued on Jan. 21, 2020].
Mindell, Joseph A. et al., "Accurate Determination of Local Defocus and Specimen tilt in Electron Microcopy," Journal of Structural Biology, vol. 142, pp. 334-347, 2003 [Cited in Parent U.S. Pat. No. 10,537,599 issued on Jan. 21, 2020].
Extended European search report dated Jul. 1, 2019 for European application No. 16871597.7 [Cited in Parent U.S. Pat. No. 10,537,599 issued on Jan. 21, 2020].
"A GeneChip? Human Genome Arrays" Affymetrix Datasheet, pp. 1-4, Jan. 1, 2003 [Cited in Parent U.S. Pat. No. 10,537,599 issued on Jan. 21, 2020].
Micaela Vargas et al., PLOS I One Aug. 2012, vol. 7, Issue 8, pp. 1-4 [Cited in Parent U.S. Pat. No. 10,537,599 issued on Jan. 21, 2020].
QuantiiFeron—TB Gold (QFT) ELISA Package Insert published by QIAGEN by Aug. 2016, pager 1-36 [Cited in Parent U.S. Pat. No. 10,537,599 issued on Jan. 21, 2020].

* cited by examiner

SENECA VALLEY VIRUS (SVV) CELLULAR RECEPTOR TARGETED ONCOTHERAPY

CROSS REFERENCE TO RELATED APPLICATIONS

The present application is a continuation of U.S. National Phase Patent Application Ser. No. 15/780,898 filed on Jun. 1, 2018 and relates to and claims the benefit and priority from International Patent. Application No, PCT/US2016/064679 filed on. Dec. 2, 2016, which relates to and claims priority from U.S. Patent Application No. 62/262,242, filed on Dec. 2, 2015, the entire disclosures of which are incorporated herein by reference in their entireties.

This invention was made with government support under T32CA009243 and P30 CA008748 awarded by National Institute of Health. The government has certain rights in the invention.

FIELD

The present application generally relates to methods of treatment for cancer using an oncolytic virus therapy comprising infection with a virus which targets a specific cellular receptor found on certain tumor cells.

BACKGROUND

Seneca Valley Virus (SVV), a recently discovered oncolytic picornavirus, selectively infects cancers with neuroendocrine features, such as small cell lung cancer (SCLC) and pediatric neuroendocrine solid tumors. These cancers constitute a major cause of morbidity and mortality—SCLC alone is responsible for approximately 30,000 deaths annually in the US Relative to other oncolytic viruses in clinical evaluation, SVV is notable for its small size, exceptionally rapid doubling time, high selectivity for neuroendocrine cancer cells, and the absence of preexisting neutralizing antibodies in patients. Previous studies in multiple preclinical mouse models confirmed the ability of SVV to home to tumor through the vasculature, resulting in potent anticancer efficacy. Phase I clinical trials testing SVV as a virotherapy in patients with neuroendocrine cancers, including SCLC, showed high levels of sustained viral replication in SCLC patients, even after the production of neutralizing antibodies to SVV, and confirmed the ability of SVV to selectively infect cancer cells after intravenous administration. Clinical development of this agent has been hampered relative to that of other oncolytic viruses by a lack of understanding of cellular determinants of infection for this new virus, most notably including identification of the cellular receptor for SVV.

Defining determinants of SVV permissivity, including identification of the viral receptor, would substantially facilitate clinical development by focusing on patients who could ultimately benefit from SVV virotherapy. The present application discloses anthrax toxin receptor 1 (ANTXR1) protein as the receptor for SVV utilizing two complementary genome-wide loss-of-function screens. ANTXR1 interacts directly and specifically with SVV. This interaction is required for SVV binding to permissive cells, and ANTXR1 expression is essential for SVV infection. The present application defines a clinically tractable predictive biomarker of SVV permissivity, and identifies ANTXR1 as the high-affinity cellular receptor for SVV in neuroendocrine cancers.

SUMMARY

One aspect of the application is a method for selecting a cancer patient for treatment with Seneca Valley Virus (SVV), comprising: determining expression level of ANTXR1 in a cancerous tissue obtained from the cancer patient; and designating the cancer patient as a candidate for treatment with SVV if normal levels or elevated levels of ANTXR1 expression is detected in the cancerous tissue. In a particular embodiment, the cancer patient is a patient with small cell lung cancer, neuroblastoma, retinoblastoma, medulloblastoma, rhabdomyosarcoma or pediatric neuroendocrine solid tumor. In another embodiment, the cancer patient is a patient with small cell lung cancer. In a further embodiment, the expression level of ANTXR1 in the cancerous tissue is determined at transcriptional level. In an additional embodiment, the expression level of ANTXR1 in the cancerous tissue is determined at a translational level.

In a further embodiment of the application, the method further comprises the step of determining the expression level of one or more biomarkers in the innate immune response pathways in the cancerous tissue, and designating the cancer patient for treatment with SVV if (1) normal levels or elevated levels of ANTXR1 expression is detected in the cancerous tissue and (2) decreased expression levels of the one or more biomarkers in the innate immune response pathways detected in the cancerous tissue. In a particular embodiment, the innate immune response pathway is the α-interferon or β-interferon pathway.

Another aspect of the application is a method for treating cancer, comprising: determining expression level of ANTXR1 in a cancerous tissue from a patient, and administering to the patient an effective amount of SVV if normal levels or elevated levels of ANTXR1 expression is detected in the cancerous tissue. In a particular embodiment, the method further comprises determining expression level of one or more biomarkers of innate immune response pathway in the cancerous tissue; and administering to the patient an effective amount of SVV if (1) normal levels or elevated levels of ANTXR1 expression is detected in the cancerous tissue and (2) decreased levels of one or more biomarkers in the innate immune response pathway in the cancerous tissue. In a particular embodiment, the SVV is administered in combination with another therapeutic agent. In certain embodiments, the therapeutic agent is selected from the group consisting of checkpoint inhibitors, cytokines, growth factors, photosensitizing agents, radionuclides, toxins, siRNA molecules, signaling modulators, anti-cancer antibiotics, anti-cancer antibody, angiogenesis inhibitors, chemotherapeutic compound, antimetastatic compound and a combination of any thereof. In a particular embodiment, the therapeutic agent is checkpoint inhibitors. In certain embodiments, the SVV is administered by direct injection into the cancerous tissue.

A further aspect of the application is a kit for selecting a cancer patient for treatment with SVV, comprising: a reagent for the detection of expression levels of ANTXR1; and a reagent for the detection of expression levels of one or more biomarkers of the α-interferon or β-interferon pathway.

BRIEF DESCRIPTION OF THE DRAWINGS

The above and other objects and advantages of the application will be apparent upon consideration of the following detailed description, taken in conjunction with the accompanying figures and paragraphs. The following are brief descriptions of the drawings herein, which illustrate certain aspects and embodiments of the present application, but are not considered limiting in any way.

DETAILED DESCRIPTION

Figure 1:
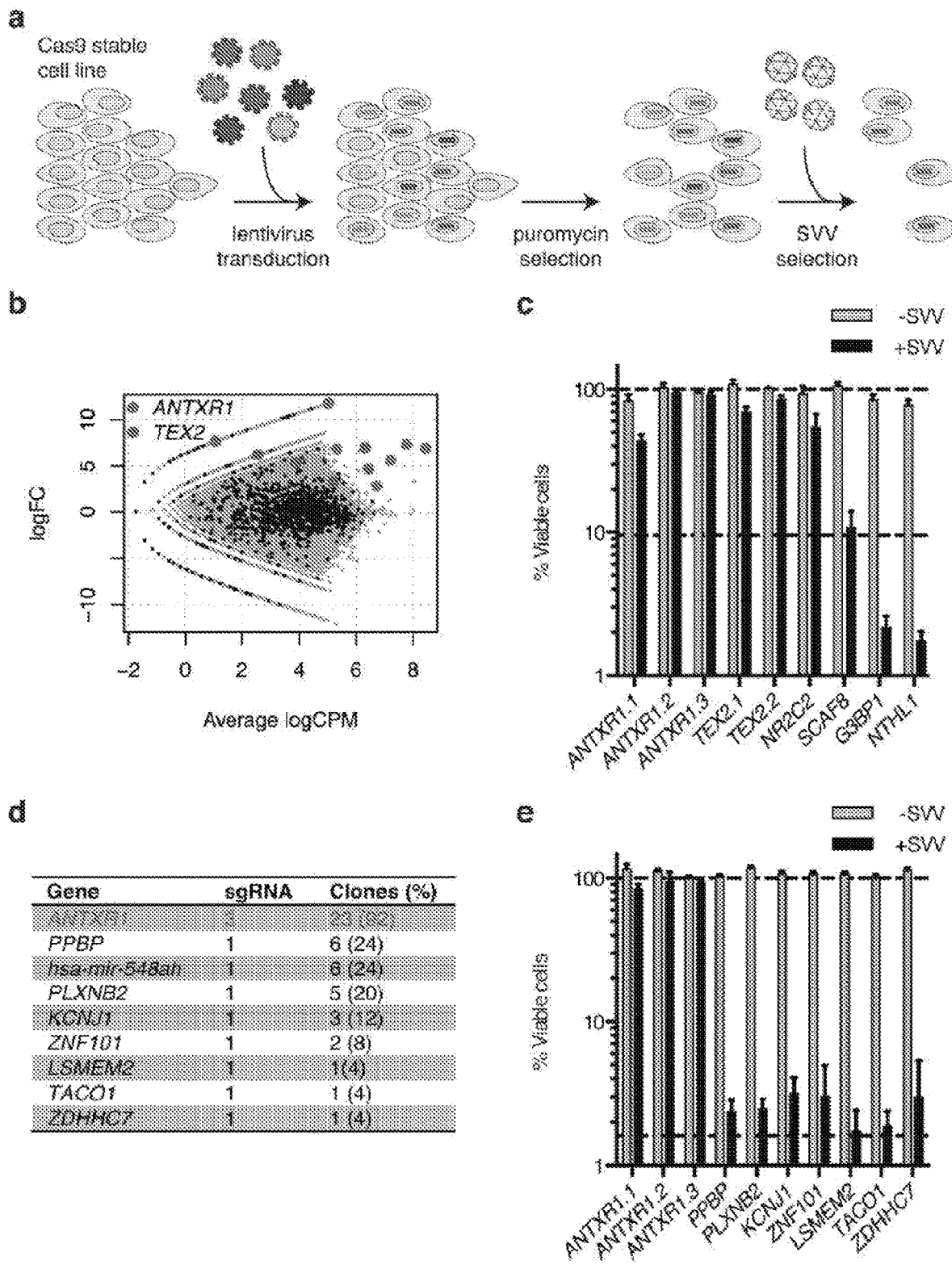
FIG. 1 shows identification of ANTXR1 as an essential host determinant for SVV. Panel a) Depiction of genome wide CRISPR knockout (GeCKO) screen workflow. After lentiviral transduction of the sgRNA library, transduced cells were selected by puromycin. Cells were then challenged with SVV to select for resistant cells. Panel b) The screen identified ANTXR1 (blue) and TEX2 (red) as the most significant hits. Non-targeting control sgRNAs are highlighted in black. Panel c) HAP 1 cells were transduced with individual sgRNAs identified from the HAP1 GeCKO screen. Cell viability was assayed in the absence (light grey) or presence (black) of SVV. Each bar corresponds to average of 6 replicates with error bars representing standard deviation. Dashed lines indicate parental HAP1 cell viability in the absence and presence of SVV. Panel d) Table of sgRNAs identified in the H446 GeCKO screen. Twenty-five H446 colonies were isolated and the lentiviral insert sequenced by Sanger sequencing. Multiple sgRNAs were identified to target the gene ANTXR1. Panel c) H446 cells were transduced with individual sgRNAs identified in the 25 H446 GeCKO screen colonies. Cell viability was tested in the absence (light grey) or presence (black) of SVV. Parental H446 cell viability in the absence and presence of SVV indicated with dashed lines. Each bar corresponds to average of 6 replicates with error bars representing standard deviation.

Some modes for carrying out the present invention are presented in terms of its aspects, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the enclosed paragraphs. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

ANTXR1 is a Targetable Cellular Receptor for SVV on Tumors

The ANTXR1 functions as one of the two receptors for the *Bacillus anthracis* toxin. SVV is unique among known viruses in using ANTXR1, or any related protein, as a primary receptor. In contrast to a number of previously identified receptors of other picornaviruses, ANTXR1 is not a member of the immunoglobulin superfamily (IgSF) of receptors. Although ANTXR1 shares common features to the IgSF receptors in being a single-pass transmembrane glycoprotein, it may be unique in its role as a receptor to both a mammalian virus and a bacterial toxin.

As disclosed herein, ANTXR1 is frequently expressed on the surface of tumor cells compared to normal cells. Efforts to develop a therapeutic antibody targeting ANTXR1 expressed in tumor endothelium have been hampered by cross-reactivity of the antibody to ANTXR2. The exquisite selectivity of SVV for ANTXR1 and the medium resolution cryo-EM structure described herein will enable future therapeutic development in the antibody space for both anti-angiogenic purposes and a potentially novel target for select neuroendocrine cancers. The gene expression data herein that beyond expression of ANTXR1, cancer cell defects in the innate immune response are important determinants of successful SVV replication. This feature is not unique to SVV and may be a shared requirement for success of many oncolytic viruses. Defects in innate immune response pathways are common in cancers; SCLC in particular has been shown to frequently lack key components of MHC class I antigen presentation as well as decreased expression of immune stimulatory cytokines. Both result in decreased tumor cell recognition and removal by the immune system. These features, together with ANTXR1 expression, can define a category of cancers particularly amenable to treatment with SVV. An improved understanding of how cellular innate immune response pathways dictate permissivity can identify synergistic combination strategies with therapeutic agents targeting these pathways in cancer cells.

For SVV, ANTXR1 expression can serve as a predictive biomarker for future clinical development, facilitating the identification of patients most likely to benefit from SVV virotherapy. Predictive biomarkers to guide future clinical trials is a particularly acute need for patients with SCLC. This is a highly aggressive and nearly universally lethal cancer, for which few tractable therapeutic targets have been identified. Many large scale clinical trials, conducted without biomarker selection, have failed to advance the standard of care for this disease. Carefully defined markers that would focus novel therapeutic studies on the responsive subset of patients could change this field. The identification of ANTXR1, and possibly suppressed innate immunity, as selection criteria will help define the structure of our subsequent clinical trials.

Cancers that may be treated by SVV include, but are not limited to, small cell lung cancer, neuroblastoma, retinoblastoma, medulloblastoma, rhabdomyosarcoma and other pediatric neuroendocrine solid tumors.

Definitions

As used herein, the following terms shall have the following meanings:

As used herein, the terms "cancer," "tumor," and "tumor cells," are used interchangeably, and refer to cells that exhibit relatively autonomous growth, so that they exhibit an aberrant growth phenotype characterized by a significant loss of control of cell proliferation. Neoplastic cells can be malignant or benign. According to the present invention, one type of preferred tumor cells are those with neurotropic properties As used herein, the term "virus," is to be understood broadly—for example—as meaning infectious viral particles that are formed when, e.g., a viral vector is transduced or transfected into an appropriate cell or cell line for the generation of infectious particles, or in particular SVV is used to infect a subject in need of treatment.

As used herein, the terms "derivative," "mutant," "variant" and "modified" are used interchangeably to generally indicate that a derivative, mutant, variant or modified virus can have a nucleic acid or amino acid sequence difference in respect to a template viral nucleic acid or amino acid sequence. For example, a SVV derivative, mutant, variant or modified SVV may refer to a SVV that has a nucleic acid or amino acid sequence difference with respect to the wild-type SVV nucleic acid or amino acid sequence of ATCC Patent Deposit Number PTA-5343.

As used herein, "combination therapy" refers to a treatment in which a subject is given two or more therapeutic agents, such as at least two or at least three therapeutic agents, for treating a single disease. For purposes herein, a combination therapy can include a treatment regime that includes administration of an oncolytic virus and another anti-cancer agent, each for treating the same hyperproliferative disease or conditions, such as the same tumor or cancer.

As used herein, the terms "biomarker" and "infectious agent-associated biomarker" are used interchangeably with reference to any molecular entity that can be used as an indicator of sensitivity to SVV (the "infectious agent"), in particular this refers to the increased expression in tumor cells of ANTXR1, and the correlated down-regulation in such tumor cells of the innate immune response pathways, such as those associated with gamma-interferon. The biomarker may be any detectable protein, nucleic acid, such as an mRNA or microRNA, lipid, or any product present and/or differentially expressed in in tumor biopsy samples whose presence and/or concentration reflects the sensitivity to SVV of a tumor in a subject. In molecular terms, biomarkers may be detected and quantitated in a subject using genomics, proteomics technologies or imaging technologies.

Methods for Patient Screening

One aspect of the present application relates to a method for selecting cancer patient for SVV treatment. The method comprises the steps of determining expression level of ANTXR1 in a cancerous tissue from a patient and designating the patient as a candidate for treatment with SVV if normal levels or elevated levels of ANTXR1 expression is detected in the cancerous tissue.

Analysis may be based on identifying the presence, absence and/or altered expression profiles of ANTXR1 in the isolated cancerous tissue samples. The analysis may carried out by comparing the expression profiles of ANTXR1 in a cancerous tissue sample to an normal expression profile of ANTXR1 stored in a database.

In some embodiment, the method further comprises the step of determining the expression profile of one or more other biomarkers in the cancerous tissue sample. In one embodiment, the one or more other biomarkers are biomarkers involved in the innate immune response pathways, including but not limited to the α-interferon or β-interferon pathways. In some embodiments, the method further comprises the step of designating the patient as a candidate for treatment with SVV if (1) normal levels or elevated levels of ANTXR1 expression is detected in the cancerous tissue and (2) decreased levels of one or more biomarkers in the innate immune response pathways in the cancerous tissue The term "increased level" refers to an expression level that is higher than a normal or control level customarily defined or used in the relevant art. For example, an increased level of immunostaining of a preparation from a tumor biopsy sample is a level of immunostaining that would be considered higher than the level of immunostaining of a control preparation by a person of ordinary skill in the art. As used herein, the described biomarker may exhibit increased expression levels of at least 10%, at least 20%, at least 30%, at least 40%, at least 50%, at least 80%, at least 100%, at least 2-fold, at least 3-fold, at least 5-fold, at least 10-fold, at least 50-fold or at least 100-fold increase or more relative to a suitable reference level.

The term "decreased level" refers to an expression level that is lower than a normal or control level customarily defined or used in the relevant art. As used herein, the described biomarkers may exhibit decreased expression levels of at least at least 10%, at least 20%, at least 30%, at least 40%, at least 50%, at least 80%, at least 100%, at least 2-fold, at least 3-fold, at least 5-fold, at least 10-fold, at least 50-fold or at least 100-fold decrease or more relative to a suitable reference level.

The term "expression level of a biomarker" may be measured at the transcription level, in which case the presence and/or the amount of a polynucleotide is determined, or at the translation level, in which case the presence and/or the amount of a polypeptide is determined.

Detection of expression of ANTXR1 or other biomarkers may be carried out at the transcription level or translation level using any methodology suitable for identifying an infectious agent-associated biomarker, including but not limited to immunohistochemistry, Western blot, ELISA, HPLC, FPLC, mass spectrometry (MS), protein sequencing, antibody array, RTPCR, quantitative RTPCR, nucleotide sequencing, oligonucleotide microarray and combinations thereof.

In some embodiments, the expression of ANTXR1 and/or other biomarkers is detected by immunohistochemistry. Briefly, a biopsy sample from a subject is contacted with an antibody that specifically binds to ANTXR1 and/or other biomarkers. After incubating the sample with antibodies, the sample is washed and the antibody-biomarker complex formed can be detected. This can be accomplished by incubating the washed sample with a detection reagent. This detection reagent may be a second antibody which is labeled with a detectable label, for example. Exemplary detectable labels include magnetic beads (e.g., DYNABEADS™), fluorescent dyes, radiolabels, enzymes (for example, horse radish peroxidase, alkaline phosphatase and others commonly used in an ELISA), and colorimetric labels such as colloidal gold or colored glass or plastic beads.

In certain embodiments, ANTXR1 and/or other biomarkers are detected using enzyme-linked immunosorbent assay (ELISA) which is typically carried out using antibody coated assay plate or wells. Commonly used ELISA assay employs either a sandwich immunoassay or a competitive binding immunoassay.

A sandwich ELISA may be used to capture, detect, characterize and quantify tissue cells from small quantities of tumor biopsy samples. A sandwich ELISA employs two antibodies, which bind to different sites on the antigen or ligand. The primary antibody, which is highly specific for the antigen, is attached to a solid surface. The antigen is then added followed by addition of a second antibody referred to as the detection antibody. The detection antibody binds the antigen to a different epitope than the primary antibody. Each of these antibodies may be directed to a different marker epitope on the same or different proteins, whereby the primary antibody captures the protein therefrom via the first protein and the detection antibody facilitates quantitation of a protein bound thereto. As a result, the protein therefrom is "sandwiched" between the two antibodies.

The binding affinity for the antigen (via antibodies) is usually the main determinant of immunoassay sensitivity. As the antigen concentration increases the amount of binding agent bound increases leading to a higher measured response. The standard curve of a sandwich-binding assay has a positive slope. To quantify the extent of binding different reporters can be used. Typically an enzyme is attached to the secondary antibody which must be generated in a different species than primary antibodies (i.e., if the primary antibody is a rabbit antibody than the secondary antibody would be an anti-rabbit from goat, chicken, etc., but not rabbit). The substrate for the enzyme is added to the reaction that forms a colorimetric readout as the detection signal. The signal generated is proportional to the amount of target antigen present in the sample. The antibody linked reporter used to measure the binding event determines the detection mode. A spectrophotometric plate reader may be used for colorimetric detection. Several types of reporters have been developed in order to increase sensitivity in an immunoassay. For example, chemiluminescent substrates have been developed which further amplify the signal and can be read on a luminescent plate reader. Also, a fluorescent readout may be obtained where the enzyme step of the assay is replaced with a fluorophore tagged antibody. This readout is then measured using a fluorescent plate reader.

In some embodiments, the antibody is attached to a solid support to facilitate washing and subsequent isolation of the antigen-antibody complex, prior to contacting the antibody with a sample. Examples of solid supports include glass or plastic in the form of a microtiter plate, a stick, a bead, or a microbead. Examples of solid supports encompassed herein include those formed partially or entirely of glass (e.g., controlled pore glass), polysaccharides (e.g., agarose), polyacrylamides, silicones, and plastics such as polystyrene, polypropylene and polyvinyl alcohol.

In some embodiments, ANTXR1 and/or other biomarkers are detected using an antibody microarray panel containing immobilized ANTXR1-specific and/or other biomarkers-specific antibodies on a substrate surface. The microarray can be used in a "sandwich" assay in which the antibody on the microarray captures ANTXR1 and/or other biomarkers in the test sample and the captured marker is detected by a labeled secondary antibody that specifically binds to the captured marker. In a preferred embodiment, the secondary antibody is biotinylated or enzyme-labeled. The detection is achieved by subsequent incubation with a streptavidin-fluorophore conjugate (for fluorescence detection) or an enzyme substrate (for colorimetric detection).

In another embodiment, the antibody microarray provides a competitive immunoassay. Briefly, a microarray comprising immobilized anti-marker antibodies is incubated with a test sample in the presence of a labeled ANTXR1 and/or other biomarker standard. The labeled ANTXR1 and/or other biomarkers compete with the unlabeled ANTXR1 and/or other biomarkers in the test sample for the binding to the immobilized antigen-specific antibody. In such a competitive setting, an increased concentration of ANTXR1 and/or other biomarkers in the test sample would lead to a decreased binding of the labeled ANTXR1 and/or other biomarker standard to the immobilized antibody and hence a reduced signal intensity from the label.

In certain embodiments, ANTXR1 and/or other biomarkers are detected using an oligonucleotide microarray for detecting and quantitating mRNA expression level(s). An oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that is used as a probe to hybridize a cDNA or cRNA sample under high-stringency conditions. Probe-target hybridization is usually detected and quantified by fluorescence-based detection of fluorophore-labeled targets to determine relative abundance of nucleic acid sequences in the target. The oligonucleotide probes are typically attached to a solid surface by a covalent bond to a chemical matrix (via epoxy-silane, amino-silane, lysine, polyacrylamide or others). The solid surface can be glass or a silicon chip or microscopic beads. Oligonucleotide arrays are different from other types of microarray only in that they either measure nucleotides or use oligonucleotide as part of its detection system.

A microarray panel can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.) or Assay 1200™. Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up the whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

Treatment Methods

Another aspect of the present application relates to a method for treating cancer. The method comprises the steps of determining expression level of ANTXR1 in a cancerous tissue from a patient, and administering to the patient an effective amount of SVV if normal levels or elevated levels of ANTXR1 expression is detected in the cancerous tissue. As used herein, the term "SVV" encompass wild type SVV, SVV derivatives, mutants, variants or modified SVV in the discussion below. In some embodiments, the method further comprises the step of determining expression level of one or more biomarkers of innate immune response pathways in the cancerous tissue and administering to the patient an effective amount of SVV if (1) normal levels or elevated levels of ANTXR1 expression is detected in the cancerous tissue and (2) decreased levels of one or more biomarkers in the innate immune response pathways in the cancerous tissue.

Administration

SVV is administered to a host or subject in an amount that is effective to inhibit, prevent or destroy the growth of the tumor cells through replication of the virus in the tumor cells. Methods that utilize SW for cancer therapy include systemic, regional or local delivery of the virus at safe, developable, and tolerable doses to elicit therapeutically useful destruction of tumor cells. Even following systemic administration, the therapeutic index for SVV is at least 10, preferably at least 100 or more preferably at least 1000. In general, SVV is administered in an amount of between $10^7$ and $1\times10^{11}$ vp/kg. The exact dosage to be administered is dependent upon a variety of factors including the age, weight, and sex of the patient, and the size and severity of the tumor being treated. The viruses may be administered one or more times, which may be dependent upon the immune response potential of the host. Single or multiple administrations of the compositions can be carried out with dose levels and pattern being selected by the treating physician. If necessary, the immune response may be diminished by employing a variety of immunosuppressants, so as to permit repetitive administration and/or enhance replication by reducing the immune response to the viruses. Anti-cancer viral therapy may be combined with other anti-cancer protocols. Delivery can be achieved in a variety of ways, employing liposomes, direct injection, catheters, topical application, inhalation, intravenous delivery, etc. Further, a DNA copy of the SVV genomic RNA, or portions thereof, can also be a method of delivery, where the DNA is subsequently transcribed by cells to produce SVV virus particles or particular SVV polypeptides.

SVV is typically administered at a therapeutically effective dose. A therapeutically effective dose refers to that amount of the virus that results in amelioration of symptoms or a prolongation of survival in a patient. Toxicity and therapeutic efficacy of viruses can be determined by standard procedures in cell cultures or experimental animals, e.g., for determining the $LD_{50}$ (the dose lethal to 50% of the population of animals or cells; for viruses, the dose is in units of vp/kg) and the $ED_{50}$ (the dose—vp/kg—therapeutically effective in 50% of the population of animals or cells) or the $EC_{50}$ (the effective concentration—vp/cell (see Table 1 for example)—in 50% of the population of animals or cells). The dose ratio between toxic and therapeutic effects is the therapeutic index and it can be expressed as the ratio between $LD_{50}$ and $ED_{50}$ or $EC_{50}$. Viruses which exhibit high therapeutic indices are preferred. The data obtained from these cell culture assays and animal studies can be used in formulating a range of dosage for use in human. The dosage of viruses lies preferably within a range of circulating concentrations that include the $ED_{50}$ or $EC_{50}$ with little or no toxicity. The dosage may vary within this range depending upon the dosage form employed and the route of administration utilized.

Formulation

The present application further relates to a pharmaceutical composition comprising the virus and a pharmaceutically acceptable carrier. Such compositions, which can comprise an effective amount of SVV in a pharmaceutically acceptable carrier, are suitable for local or systemic administration to individuals in unit dosage forms, sterile parenteral solutions or suspensions, sterile non-parenteral solutions or oral solutions or suspensions, oil in water or water in oil emulsions, and the like. Formulations for parenteral and non-parenteral drug delivery are known in the art. Compositions also include lyophilized and/or reconstituted forms of SVV. Acceptable pharmaceutical carriers are, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.) and phosphate-buffered saline and sucrose. The selection of a suitable pharmaceutical carrier is deemed to be apparent to those skilled in the art from the teachings contained herein. These solutions are sterile and generally free particulate matter other than SVV. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, etc. Excipients that enhance infection of cells by SVV may be included.

The SVV may be present in the composition in multidose and single dosage amounts, including, but not limited to between or between about $1\times10^5$ and $1\times10^{12}$ pfu, $1\times10^6$ to $1\times10^{10}$ pfu, or $1\times10^7$ to $1\times10^{10}$ pfu, each inclusive, such as at least or about at least or $1\times10^6$, $1\times10^7$, $1\times10^8$, $1\times10^9$, $2\times10^9$, $3\times10^9$, $4\times10^9$, $5\times10^9$ pfu, $1\times10^{10}$ pfu.

The volume of the composition can be any volume, and can be for single or multiple dosage administration, including, but not limited to, from or from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

The infectivity of the SVV can be manifested, such as by increased titer or half-life of the oncolytic virus when exposed to a bodily fluid, such as blood or serum. Infectivity can be increased by any amount, including, but not limited to, at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold Combination Therapy In some embodiments, SVV treatment is used in combination with immunotherapy. Suitable immunotherapies that may be used in combination with SVV include, but are not limited to, the use of checkpoint inhibitors, such as Nivolumab, Pembrolzumab, and Ipilimumab. SVV may be administered in combination with an immunotherapy or in sequence with it (e.g., before or after). The combinations can also include additional compositions, which include additional agents in one or both of the compositions, such as another active agent, such as an anticancer compound or therapeutic agent or another different oncolytic virus, and/or a diagnostic agent. Adjunct therapies are also contemplated in the present application as a form of therapy in which SVV may be used in combination with other agents. As used herein, "adjunct therapy" refers to a treatment in which another treatment is used with a primary treatment to assist or enhance the primary treatment. Thus, it is a treatment that is given in addition to the primary, main or initial treatment. The adjunct therapy increases the effectiveness of the primary treatment in treating a condition. For purposes herein, treatment with an oncolytic virus is the primary or main treatment, and one or more different treatments are employed to increase the effectiveness of the oncolytic virus therapy, such as by increasing infectivity. Exemplary of such agents are a therapeutic compound, an agent that increases virus infectivity, a therapeutic or diagnostic virus, an antiviral or chemotherapeutic agent, or an agent or compound for modulation of gene expression of endogenous or heterologous genes encoded by the virus.

Also provided are combinations of the compositions that contain the virus formulated for delivery as one composition, and a second composition containing an additional active agent such as, but not limited to a therapeutic compound, an agent that increases virus infectivity, a therapeutic or diagnostic virus, an antiviral or chemotherapeutic agent, or an agent or compound for modulation of gene expression of endogenous or heterologous genes encoded by the virus. Additional active agents include anti-cancer agents, and also agents that modulate or alter or improve properties of the virus. Therapeutic compounds include, for example, any selected from among a cytokine, growth factor, photosensitizing agent, radionuclide, toxin, siRNA molecule, enzyme/pro E drug pair, anti-metabolite, signaling modulator, anti-cancer antibiotic, anti-cancer antibody, angiogenesis inhibitor, chemotherapeutic compound, antimetastatic compound and a combination of any thereof.

In particular the additional agent for inclusion in the combination and also in any composition provided herein or as part of any combination provided herein, an agent that modulates or alters or improves a property of the virus, such as an agent that increases infectivity of the virus. These include agents that alter the immune response to the virus so that less is cleared upon administration. Additional agents include agents such as, for example, complement inhibitors, agents that inhibit complement activation or the activity of any protein in a complement pathway, such as, inhibition of the activity of any of complement proteins C1, C2, C3, C4, C5, C5a, C5aR, C3aR, Factor B, Factor P, Clq and MBP. Such agents are known to those of skill in the art, and include, for example, include antibodies specific for one or more of these proteins. Exemplary inhibitors include, for example, cobra venom factor (CVF), heparin, TA 106, TNX-234, anti-properdin, C1-INH, a compstatin or derivative or analog thereof, soluble CR1, K76COOH, eculizumab, pexelizumab, TSA12/22, MSA12/22, ARC 1005, TNX-558, NOX-D19, PMX-53, PMX-201, PMX-205, neutrazumab, and variants, analogs or derivatives thereof that inhibit a complement activity.

Kit

Another aspect of the present application relates to a kit for selecting cancer patients that are likely to be responsive to treatment with SVV is contemplated. Such a kit may include a reagent for the detection of expression levels of ANTXR1 in cancerous tissue, and one or more reagents for the detection of expression of one or more biomarkers in the innate immune response pathways, including but not limited to the α-interferon or β-interferon pathways. In some embodiments, the reagent for the detection of expression levels of ANTXR1 is an anti-ANTXR1 antibody or a pair of ANTXR1-specific oligonucleotide primers.

Below are disclosed methods, materials and procedures for the practice of an embodiment of the invention. One of ordinary skill will understand that the invention is not limited to the below disclosed methods, materials and procedures. One of ordinary skill will understand that the invention may be used in conjunction with therapeutic and diagnostic approaches relevant to specific cell types in both plants and mammals. Further aspects and advantages of the application will appear from the following description taken together with the accompanying drawings

EXAMPLES

Example 1: Materials and Methods

Reagents and Bacterial Strains

Polymerase chain reactions (PCRs) were carried out using a GeneAmp PCR System 9700 Thermocycler (Applied Biosystems). PCR fragments were purified using QIAquick PCR Purification Kit (Qiagen). Genomic DNA was extracted using the DNeasy Blood and Tissue Kit (Qiagen). Competent DH10B and Stbl3 cells were purchased from Invitrogen. Plasmids were isolated and purified from bacteria using QIAquick Spin Miniprep Kit (Qiagen) Sanger sequencing for individual clones and plasmids was performed by Genewiz, Inc. Nucleotide and protein sequence alignments were performed in Geneious Pro 4.7.6. The foregoing merely illustrates the principles of the disclosure.

Cell Lines and Viruses

All cell culture media and solutions were produced by the Memorial Sloan Kettering Cancer Center (MSKCC) Media Prep core facility. HAP1 cells were purchased from Haplogen GmbH and maintained in Iscove's Modified Dulbecco's Medium (IMDM) supplemented with 10% fetal calf serum. TC-71 cells were obtained from Children's Oncology Group (COG) Cell Culture Repository and maintained in IMDM supplemented with 10% fetal bovine serum and 1×ITS supplement. All other cell lines used in this study were purchased from ATCC. HEK 293T/17 cells were maintained in high glucose Dulbecco's Modified Eagle Medium (DMEM HG) supplemented with 10% fetal calf serum and 1 mM sodium pyruvate. All additional lines were maintained in RPMI 1640 supplemented with 10% fetal calf serum and 10 mM HEPES. All cell lines are routinely confirmed by STR analysis and confirmed *mycoplasma* negative by DDC Medical. SVV and SVV-GFP was cultured, purified, and titered as previously described (Reddy, P. S., et al. Seneca Valley virus, a systemically deliverable oncolytic picornavirus, and the treatment of neuroendocrine cancers. J Natl Cancer Inst 99, 1623-1633 (2007); Poirier, J. T., et al. Characterization of a full-length infectious cDNA clone and a GFP reporter derivative of the oncolytic picornavirus SVV-001. J Gen Virol 93, 2606-2613 (2012)).

Human GeCKO v2 Library

The Human GeCKO v2 library was obtained as two half libraries (Library A and B) in the lentiGuide-Puro plasmid backbone (Addgene plasmid #52962) as an inter-laboratory transfer. The MSKCC RNAi core facility amplified the pooled libraries by electroporation of Endura electrocompetent cells (Lucigen) as described previously (Shalem, O., et al. Genome-scale CRISPR-Cas9 knockout screening in human cells. Science 343, 84-87 (2014); Sanjana, N. E., Shalem, O. & Zhang, F. Improved vectors and genome-wide libraries for CRISPR screening. Nature methods 11, 783-784 (2014)). Plasmid DNA libraries were used as a template in a nested PCR to first amplify the section of the plasmid containing the sgRNA (Table 1 (Oligonucleotide list for primers used in cloning and sequencing for CRISPR constructs and ANTXR1 expression constructs. Numbers correspond to oligonucleotide identity in the main text. Primer name describes the sgRNA gene target or product the primers will eventually create. Oligonucleotides shown from 5' to 3'); SEQ ID NOS. #1-2) and subsequently to add Illumina sequencing adaptors and barcodes (SEQ ID NOS. #3-18). The nested PCR products were then sequenced for confirmation of sgRNA representation using an Illumina HiSeq2500 (SEQ ID NOS. #19).

TABLE 1

| Name (SEQ ID NO.) | Primer Sequence |
|---|---|
| 1-lentiCRISPR v2 amplification F | 5'-CTTTAGTTTGTATGTCTGTTGCTATTATGTCTACTATTCTTTCC-3' |
| 2-lentiCRISPR v2 amplification R | 5'-AATGGACTATCATATGCTTACCGTAACTTGAAAGTATTTCG-3' |
| 3-HiSeq F#1 | 5'-AATGATACGGCGACCACCGAGATCTACACTCTTTCCCTACACGACGCTCT TCCGATCTTTCTTGTGGAAAGGACGAAACACCG-3' |
| 4-HiSeq F#2 | 5'-AATGATACGGCGACCACCGAGATCTACACTCTTTCCCTACACGACGCTCT TCCGATCTATTCTTGTGGAAAGGACGAAACACCG-3' |

TABLE 1-continued

| Name (SEQ ID NO.) | Primer Sequence |
| --- | --- |
| 5-HiSeq F#3 | 5'-AATGATACGGCGACCACCGAGATCTACACTCTTTCCCTACACGACGCTCTTCCGATCTGATTCTTGTGGAAAGGACGAAACACCG-3' |
| 6-HiSeq F#4 | 5'-AATGATACGGCGACCACCGAGATCTACACTCTTTCCCTACACGACGCTCTTCCGATCTCGATTCTTGTGGAAAGGACGAAACACCG-3' |
| 7-HiSeq R#1 | 5'-CAAGCAGAAGACGGCATACGAGATCGTGATGTGACTGGAGTTCAGACGTGTGCTCTTCCGATCTTCTACTATTCTTTCCCCTGCACTGT-3' |
| 8-HiSeq R#2 | 5'-CAAGCAGAAGACGGCATACGAGATACATCGGTGACTGGAGTTCAGACGTGTGCTCTTCCGATCTTCTACTATTCTTTCCCCTGCACTGT-3' |
| 9-HiSeq R#3 | 5'-CAAGCAGAAGACGGCATACGAGATGCCTAAGTGACTGGAGTTCAGACGTGTGCTCTTCCGATCTTCTACTATTCTTTCCCCTGCACTGT-3' |
| 10-HiSeq R#4 | 5'-CAAGCAGAAGACGGCATACGAGATTGGTCAGTGACTGGAGTTCAGACGTGTGCTCTTCCGATCTTCTACTATTCTTTCCCCTGCACTGT-3' |
| 11-HiSeq R#5 | 5'-CAAGCAGAAGACGGCATACGAGATCACTGTGTGACTGGAGTTCAGACGTGTGCTCTTCCGATCTTCTACTATTCTTTCCCCTGCACTGT-3' |
| 12-HiSeq R#6 | 5'-CAAGCAGAAGACGGCATACGAGATATTGGCGTGACTGGAGTTCAGACGTGTGCTCTTCCGATCTTCTACTATTCTTTCCCCTGCACTGT-3' |
| 13-HiSeq R#7 | 5'-CAAGCAGAAGACGGCATACGAGATGATCTGGTGACTGGAGTTCAGACGTGTGCTCTTCCGATCTTCTACTATTCTTTCCCCTGCACTGT-3' |
| 14-HiSeq R#8 | 5'-CAAGCAGAAGACGGCATACGAGATTCAAGTGTGACTGGAGTTCAGACGTGTGCTCTTCCGATCTTCTACTATTCTTTCCCCTGCACTGT-3' |
| 15-HiSeq R#9 | 5'-CAAGCAGAAGACGGCATACGAGATCTGATCGTGACTGGAGTTCAGACGTGTGCTCTTCCGATCTTCTACTATTCTTTCCCCTGCACTGT-3' |
| 16-HiSeq R#10 | 5'-CAAGCAGAAGACGGCATACGAGATAAGCTAGTGACTGGAGTTCAGACGTGTGCTCTTCCGATCTTCTACTATTCTTTCCCCTGCACTGT-3' |
| 17-HiSeq R#11 | 5'-CAAGCAGAAGACGGCATACGAGATGTAGCCGTGACTGGAGTTCAGACGTGTGCTCTTCCGATCTTCTACTATTCTTTCCCCTGCACTGT-3' |
| 18-HiSeq R#12 | 5'-CAAGCAGAAGACGGCATACGAGATTACAAGGTGACTGGAGTTCAGACGTGTGCTCTTCCGATCTTCTACTATTCTTTCCCCTGCACTGT-3' |
| 19-HiSeq seq primer | 5'-ACACTCTTTCCCTACACGACGCTCTTCCGATCT-3' |
| 20-lentiGuide F | 5'-AATGGACTATCATATGCTTACCGTAACTTGAAAGTATTTCG-3' |
| 21-lentiGuide R | 5'-CTTTAGTTTGTATGTCTGTTGCTATTATGTCTACTATTCTTTCC-3' |
| 22-ANTXR1.1 F | 5'-CACCGGGAGACACTTACATGCATGA-3' |
| 23-ANTXR1.1 R | 5'-AAACTCATGCATGTAAGTGTCTCCC-3' |
| 24-ANTXR1.2 F | 5'-CACCGCAGGAAGTGTGCTGCACCAC-3' |
| 25-ANTXR1.2 R | 5'-AAACGTGGTGCAGCACACTTCCTGC-3' |
| 26-ANTXR1.3 F | 5'-CACCGCTATTACTTTGTGGAACAGT-3' |
| 27-ANTXR1.3 R | 5'-AAACACTGTTCCACAAAGTAATAGC-3' |
| 28-G3BP1 F | 5'-CACCGCGCACTCTTTGATCCCGCTG-3' |
| 29-G3BP1 R | 5'-AAACCAGCGGGATCAAAGAGTGCGC-3' |
| 30-KCNJ1 F | 5'-CACCGCGTGTCAAACACATTCCGAC-3' |
| 31-KCNJ1 R | 5'-AAACGTCGGAATGTGTTTGACACGC-3' |
| 32-LSMEM2 F | 5'-CACCGGAGTGAATCCCTGCGCATCC-3' |
| 33-LSMEM2 R | 5'-AAACGGATGCGCAGGGATTCACTCC-3' |
| 34-NR2C2 F | 5'-CACCGAACTGACAGCCCCATAGTGA-3' |
| 35-NR2C2 R | 5'-AAACTCACTATGGGGCTGTCAGTTC-3' |

TABLE 1-continued

| Name (SEQ ID NO.) | Primer Sequence |
| --- | --- |
| 36-NTHL1 F | 5'-CACCGACAGCCCCGTGAAGCGTCCG-3' |
| 37-NTHL1 R | 5'-AAACCGGACGCTTCACGGGGCTGTC-3' |
| 38-PLXNB2 F | 5'-CACCGCTGCGGCTGGTGCGTCGTCG-3' |
| 39-PLXNB2 R | 5'-AAACCGACGACGCACCAGCCGCAGC-3' |
| 40-PPBP F | 5'-CACCGCAACTTACATCACTTCGACT-3' |
| 41-PPBP R | 5'-AAACAGTCGAAGTGATGTAAGTTGC-3' |
| 42-SCAF8 F | 5'-CACCGTAGCATACCTTGTCATCCCC-3' |
| 43-SCAF8 R | 5'-AAACGGGGATGACAAGGTATGCTAC-3' |
| 44-TACO1 F | 5'-CACCGGCGACACACCTCTAAGATAT-3' |
| 45-TACO1 R | 5'-AAACATATCTTAGAGGTGTGTCGCC-3' |
| 46-TEX2.1 F | 5'-CACCGTACCCCATTTGTATCGAGCT-3' |
| 47-TEX2.1 R | 5'-AAACAGCTCGATACAAATGGGGTAC-3' |
| 48-TEX2.2 F | 5'-CACCGCTGAATGTGTCAAAGTCGCA-3' |
| 49-TEX2.2 R | 5'-AAACTGCGACTTTGACACATTCAGC-3' |
| 50-ZDHHC7 F | 5'-CACCGGCACTTGTAGATGACTTCCC-3' |
| 51-ZDHHC7 R | 5'-AAACGGGAAGTCATCTACAAGTGCC-3' |
| 52-ZNF101 F | 5'-CACCGTGAAATCAGATCTCACGCGC-3' |
| 53-ZNF101 R | 5'-AAACGCGCGTGAGATCTGATTTCAC-3' |
| 54-sgRNA Seq F | 5'-GACTATCATATGCTTACCGT-3' |
| 55-ANTXR1 exon2 PCR F | 5'-TGAGTCCAGTTATTGGAGAGGTC-3' |
| 56-ANTXR1 exon2 PCR R | 5'-CGAGATCTGAGAGCCCAACT-3' |
| 57-attB1 ANTXR1 cDNA F | 5'-GGGGACAAGTTTGTACAAAAAAGCAGGCTTAACCATGGCCACGGCGGAGCGGAGA-3' |
| 58-attB2 ANTXR1 cDNA R | 5'-GGGGACCACTTTGTACAAGAAAGCTGGGTATCATCAAGCGTAGTCTGGGACG-3' |
| 59-ANTXR1 truncation Δ33-85 F | 5'-GTTGTTCCTCGGGTGGACCTGCGTCCCCCTTGCCCGGCGCA-3' |
| 60-ANTXR1 truncation Δ33-85 R | 5'-GGGCAAGGGGGACGCAGGTCCACCCGAGGAACAACCTTAAT-3' |
| 61-ANTXR1 truncation Δ33-140 F | 5'-GACGCTGGCTGTCCTGTACCTGCGTCCCCCTTGCCCGGCGC-3' |
| 62-ANTXR1 truncation Δ33-140 R | 5'-GGGCAAGGGGGACGCAGGTACAGGACAGCCAGCGTCATCAT-3' |
| 63-ANTXR1 truncation Δ33-184 F | 5'-AATCCGGGCCAGCTGTGTCCTGCGTCCCCCTTGCCCGGCGC-3' |
| 64-ANTXR1 truncation Δ33-184 R | 5'-GGGCAAGGGGGACGCAGGACACAGCTGGCCCGGATTGCGGA-3' |
| 65-ANTXR1 truncation Δ33-298 F | 5'-TGCAGCTTTCATGCCAACCCTGCGTCCCCCTTGCCCGGCGC-3' |
| 66-ANTXR1 truncation Δ33-298 R | 5'-GGGCAAGGGGGACGCAGGGTTGGCATGAAAGCTGCACTCCA-3' |

Individual sgRNA Plasmids

The lentiCRISPR v2 plasmid, which expresses a single sgRNA under the hU6 promoter and the WT Cas9 nuclease under the EFS promoter, was a gift from Feng Zhang (Addgene plasmid #52961). Oligos containing the gene targeting sgRNA with 5' overhang BsmBI digestion sites were synthesized by Sigma Aldrich (SEQ ID NOS. #22-53). The oligos were annealed and inserted into the lentiCRISPR v2 backbone as described above herein. sgRNA sequences and plasmids were confirmed by Sanger sequencing.

Inducible ANTXR1 Expression Plasmid Construction

To create an inducible ANTXR1 expression lentiviral plasmid, a plasmid was obtained expressing a full-length ANTXR1 cDNA as an inter-laboratory transfer. The plasmid (ANTXR1-HA), which constitutively expresses the ANTXR1 cDNA fused to a C-terminal influenza virus hemagglutinin (HA) tag, was used as a template in PCR with primers incorporating Gateway attB1 and attB2 cloning sequences (SEQ ID NOS. #57-58). The PCR product was purified and subsequently used in a BP reaction with the Gateway destination vector, pDONR221 (Invitrogen), transformed into DH10B cells, and selected on LB agar plates supplemented with 50 µg/ml kanamycin (Sigma Aldrich). The plasmid containing the PCR fragment was purified and used in an LR reaction with pInducer20, another inter-laboratory transfer (Addgene plasmid #44012). The recombinant plasmid was transformed into Stbl3 cells and selected on LB agar plates supplemented with 100 µg/ml carbenicillin (Sigma). The purified plasmid, containing a doxycycline (Dox) inducible ANTXR1 cDNA with the HA fusion tag, was confirmed by Sanger sequencing and used to produce lentivirus for the creation of stable cell lines.

ANTXR1-HA Expression Plasmid Truncation Cloning

The full-length ANTXR1-HA expression plasmid described above was used as a template in PCR with primers to sequentially remove regions of the N-terminal cDNA sequence (SEQ ID NOS. #59-66). Primers were designed as described previously (Hansson, M. D., Rzeznicka, K., Rosenback, M., Hansson, M. & Sirijovski, N. PCR-mediated deletion of plasmid DNA. Anal Biochem 375, 373-375 (2008)). To ensure proper localization of the resulting ANTXR1-HA protein, the cDNA sequence encoding the full signal peptide sequence was retained in the expression plasmid. PCR reactions were incubated with DpnI (New England Biolabs) to remove the template plasmid, transformed into Stbl3 cells, and selected on LB agar plates supplemented with 100 µg/ml carbenicillin (Sigma). The purified plasmids, containing N-terminal ANTXR1 truncations, were confirmed by Sanger sequencing.

Lentivirus Production

The lentiviral packaging plasmids pMD2.G (Addgene plasmid #12259) and psPAX2 (Addgene plasmid #12260) were gifts from Didier Trono. All transfections of lentiviral plasmids were performed as follows unless otherwise stated: Lentiviral plasmids were transfected at a 3:2:1 DNA ratio of lentiviral plasmid:psPAX2:pMD2.G in 1 mg/mL polyethylinimine (PEI; Sigma Aldrich) at a 2:1 PEI:DNA ratio in OptiMEM (Gibco). Media was changed 16 h post transfection. Seventy-two hours post transfection the virus containing media was harvested and filtered through a 0.45 µm PDVF syringe filter (Millipore) to remove cell debris. Lentivirus aliquots were stored at −80° C.

For the human GeCKO library, 20 15 cm2 dishes (Corning) were seeded with HEK 293T/17 cells (7.0×106 per plate). The GeCKO libraries A and B were pooled 1:1 (54 µg each library) and co-transfected with psPAX2 (72 µg) and pMD2.G (36 µg) with 432 µL of 1 mg/mL PEI in 36 mL OptiMEM. The transfection mix was then divided equally among the 15 cm2 dishes. Sixteen hours post transfection, media on each dish was changed and supplemented with 1 U/mL DNase I (New England Biolabs). The media lentiviral supernatant was harvested 72 h post transfection and filtered through a 0.45 µm Stericup PVDF filter (Millipore). The virus was then pelleted by ultracentrifugation at 24,000 rpm for 2 h at 4° C. The virus pellet was resuspended in fresh DMEM and incubated overnight at 4° C. Lentivirus aliquots were stored at −80° C.

Lentiviral Transductions

All lentiviral transductions were performed as follows unless otherwise stated: Cells (1.0×106) to be transduced were plated in a 75 cm2 flask the day before transduction. Lentivirus was thawed on ice and added to OptiMEM supplemented with 32 µg/mL polybrene. After the virus-OptiMEM mix was added to the cells, additional media was added to bring the final polybrene concentration to 8 µg/mL. Media was changed 24 h after transduction to remove polybrene. Media supplemented with 0.5 µg/mL puromycin (Sigma Aldrich) or 6 µg/mL blasticidin (Fisher Scientific) was changed 48 h after transduction to select lentiCRISPRv2 or lentiCas9-Blast transduced cells, respectively. Transduced cells were maintained in media containing either puromycin or blasticidin. For Dox inducible ANTXR1 lentivirus (pInducer20-ANTXR1), the SCLC H69 and H146 cell lines were transduced and maintained in tetracycline-free (tet-free) media supplemented with 500 µg/mL G-418 (Thermo Fisher).

GeCKO Library Screen

The human GeCKO v2 library lentivirus was titered on parental HAP 1 and H446 cells as described above. Parental cells were transduced with the lentiCas9-Blast lentivirus, allowing for constitutive expression of the DNA nuclease, Cas9. The lentiCas9-Blast plasmid was a gift from Feng Zhang (Addgene plasmid #52962). Transduced cells were selected with 6 µg/mL blasticidin. HAP1-Cas9 cells (2.0×108) were seeded equally in 70 15 cm2 dishes. H446-Cas9 cells (1.5×108) were seeded into 50 15 cm2 dishes GeCKO lentivirus was thawed on ice, mixed in a total volume of 375 mL OptiMEM supplemented with 32 µg/mL polybrene, and divided equally among the HAP1-Cas9 or H446-Cas9 plates. Lentivirus was added at an MOI=0.4 transduction units/cell (TU/cell) for both screens. Additional media was added to each plate to bring the final polybrene concentration to 8 µg/mL. Media was changed 24 h post transduction to remove polybrene. The media was changed 48 h post transduction to select transduced H446-Cas9 or HAP1-Cas9 cells with 0.5 µg/mL or 1.0 µg/mL puromycin, respectively. Transduced cells were allowed to grow for 4 additional days to allow for complete knockdown of sgRNA-targeted genes. On day 7 post transduction in the HAP1 screen, 2.0×108 cells were plated at equal cell density in 40 15 cm2 dishes and infected with SVV at a MOI=1,000 vp/cell the next day. On day 7 post transduction in the H446 screen, 1.5×108 cells were plated at equal cell density in 50 15 cm2 dishes and infected with SVV at a MOI=1.0 vp/cell the next day. The remaining cells for each cell line were pooled, pelleted by centrifugation, and stored in −80° C. as the corresponding Day 7 post transduction sample. For one week post SVV infection during the HAP1 screen, 15 mL media on the infected plates were exchanged every 3 days to resupply cells with fresh media. Surviving cells were pooled, pelleted by centrifugation, and stored at −80° C. as the SVV resistant sample. For two weeks post SVV infection during the H446 screen, 10 mL media on the infected plates were exchanged every 3 days to resupply cells with fresh media. Visible colonies of surviving cells were collected by isolated trypsinization in cloning cylinders and seeded in 1 well of a 24 well plate (Corning). All colonies too small for isolation were harvested by trypsinization and pooled before expansion. Each isolated colony was ultimately expanded from a 24 well to a 75 cm2 flask as the cells were propagated. Cells from each colony were pelleted by centrifugation and stored in −80° C.

Identification of sgRNAs

For the HAP1 screen, extracted genomic DNA from Day 7 post transduction and SVV resistant population was used as a template for the GeCKO v2 library nested PCR and analyzed for sgRNA representation by Illumina HiSeq as described above. Sequenced sgRNAs were imported from raw FASTQ files, normalized for library size, then converted to log counts per million reads (logCPM). Log fold change was then calculated between control and resistant samples. Based on the distribution of non-targeting sgRNAs, we focused on genes for which ≥2 unique sgRNAs had average logCPM>6 and logFC>5. Gene-wise testing was performed by the Mann-Whitney test. Computer code available upon request.

For the H446 screen, extracted genomic DNA from each SVV resistant colony was used as a PCR template to amplify the lentiviral insert containing the gene-targeting sgRNA (SEQ ID NO. #54). The PCR product was purified then sequenced via Sanger sequencing. PCR products that contained multiple sgRNAs, as determined by Sanger sequencing, were ligated into the linearized pCR2.1 plasmid using the TA Cloning Kit (Invitrogen). The ligation reaction was transformed into DH10B cells (Invitrogen) and selected on LB agar plates supplemented 100 µg/mL carbenicillin (Fisher). Colonies from each transformation plate were isolated, amplified, and sequenced by Sanger sequencing.

CRISPR Secondary Screens

Individual targeting sgRNAs were cloned into the lentiCRISPRv2 plasmid as described above. The sgRNA plasmids were individually transfected into HEK 293T/17 cells and transduced in parental H446 or HAP1 cells as described above. Transduced H446 cells were selected with 0.5 µg/mL puromycin. Transduced HAP1 cells were selected with 1.0 µg/mL puromycin. Cells were allowed to grow for at least 7 days post transduction to allow for complete gene knockout. Cell viability was assessed by AlamarBlue fluorescent cell viability dye (ThermoFisher Scientific) as described below.

Cell Viability Assays and Analysis

Twenty-four hours prior to infection, cells (5.0×103) were seeded into black opaque 96-well plates (Corning) in 100 µL media. Plates were infected with serial dilutions of SVV from an MOI=5,000 vp/cell to MOI=5.0×10-5 vp/cell and incubated for 24-72 h. Each MOI was tested in 3-6 replicate wells with uninfected cells as controls. AlamarBlue cell viability solution was added to each well and incubated at 37° C. Fluorescence emission at 590 nm was obtained after excitation at 565 nm using a Synergy Neo plate reader (BioTek) using wells containing only media as background controls. Background fluorescence values were subtracted and replicate wells averaged to determine average fluorescence and standard deviation for each MOI of SVV. The average fluorescence value at each MOI was divided by average fluorescence value of the control wells to calculate percent cell viability. Cell viability values and standard deviations were plotted against MOI of SVV using GraphPad Prism 6 software.

Identification of ANTXR1 Indels in ANTXR1 KO Lines

Extracted genomic DNA from parental H446 cells and ANTXR1 KO mutant clones was used as a PCR template to amplify the target of the ANTXR1 sgRNA, exon 2 of the ANTXR1 gene, using sequence specific primers (SEQ ID NOS. #55-56). The PCR product was ligated into the linearized pCR2.1 plasmid using the TA Cloning Kit (Invitrogen). The ligation reaction was transformed into DH10B cells (Invitrogen) and selected on LB agar plates supplemented 100 g/mL carbenicillin (Fisher Scientific). Colonies from each transformation plate were isolated, amplified, and sequenced by Sanger sequencing. Exon 2 sequences from ANTXR1 KO lines were compared to WT H446 exon 2 sequences and ANTXR1 gene reference sequence (NG_012649.1; Pubmed) to identify indels in each cell line.

ANTXR1-KO Lines

All cell lines were transduced with ANTXR1.3 sgRNA lentiCRISPRv2 lentivirus as described above. Transduced cells in each cell line were selected with 1.0 µg/mL puromycin. Cells were allowed to grow for at least 7 days post transduction to allow for complete gene knockdown. As a negative control cell line, parental H446 cells were similarly transduced with lentiCRISPRv2 lentivirus containing an EGFP targeting sgRNA, an inter-laboratory transfer (Addgene plasmid #51764), and selected with puromycin.

H446 ANTXR1 KO mCherry Cell Line

A pLenti6 W118-mCherry lentiviral expression plasmid containing the fluorescent mCherry protein cDNA was used to produce lentivirus as described above. The H446 ANTXR1 KO 4 clone isolated from the H446 GeCKO screen was transduced with the mCherry lentivirus as described previously. Forty-eight hours after transduction, transduced cells were isolated by positive mCherry fluorescence using fluorescent activated cell sorting (FACS) with a BD FACSAria (Becton Dickinson) and subsequently cultured as a stable cell line (H446 ANTXR1 KO mCherry).

In Vivo SW-001 Efficacy

All animal experiments and procedures were carried out in accordance with the guidelines set by the Institutional Animal Care and Use Committee at Memorial Sloan Kettering Cancer Center. Female athymic nude mice, aged 6-8 weeks, were purchased from Envigo, Inc. Mice were engrafted subcutaneously with a 1:1 mixture of matrigel (Corning) and either parental H446 cells, H446 ANTXR1 KO mCherry cells, or 1:1 mix of parental: KO mCherry cells in Hanks Balanced Salt Solution (HBSS). Once tumors reached volumes of ~100 mm$^3$, mice within each cohort were randomly distributed and administered SVV-001 ($1\times10^3$ vp/kg) via intraperitoneal injection or PBS, pH 7.4 as vehicle controls. Tumor dimensions were measured with external calipers every 48 hr. Tumor volumes were estimated by the formula $V=(L\times W^2)/2$ where L is the length or diameter and W is the width. Calculated tumor averages for each cohort and standard deviations were plotted using GraphPad Prism 6 software. At the end of study, mice were euthanized, tumors excised, and analyzed by flow cytometry.

ANTXR1 Expression Experiments

Unless otherwise stated, cells were transfected and analyzed as follows: ANTXR1 rescue experiments were performed with the ANTXR1-HA expression plasmid. Cells were plated in tissue culture treated 6-well plates 24 h prior to transfection. Cells were transiently co-transfected with ANTXR1-HA and pLenti6 W118-mCherry, which constitutively expresses the fluorescent protein mCherry, in 1 mg/mL PEI in OptiMEM with untransfected cells as controls. Media was changed 16 h post transfection. The cells were then harvested for Western blot analysis or challenged with SVV-GFP for flow cytometry analysis as described below. For Western blot lysates, transfected cells were harvested 48 h post transfection and pelleted by centrifugation. Cell pellets were lysed in radioimmunoprecipitation assay (RIPA) buffer (Pierce) supplemented with IX Halt Protease and Phosphatase Inhibitor Cocktail (Pierce) and subsequently clarified by centrifugation. Protein lysates were quantified using the BCA protein assay kit (Pierce) and prepared for Western blot analysis by boiling in for 10 min at 90° C. in NuPAGE sample reducing agent and LDS sample buffer (Invitrogen). Western blots analysis was performed as described below.

For re-expression experiments in SCLC ANTXR1 KO lines, cells were transiently co-transfected with ANTXR1-HA and pLenti6 W118-mCherry expression plasmids at a 10:1 molar ratio in 1 mg/mL PEI in OptiMEM with cells transfected with mCherry alone as controls. Cells were challenged with SVV-GFP at the $TCID_{50}$ for each cell line 48 h post transfection and harvested for analysis 6 hr post SVV-GFP infection. For expression experiments in non-permissive SCLC cell lines, pInducer20-ANTXR1 transduced H69 or H146 cells were seeded in 6-well plates 16 h prior to the start of the experiment. Cells were maintained in tet-free media alone or supplemented with 1 µg/mL doxycycline for 72 h prior to the addition of SVV-GFP. Cells were incubated with SVV-GFP for 6 h then harvested for analysis. For re-expression experiments testing ANTXR1 N-terminal truncations, cells were transiently co-transfected with full-length or truncated ANTXR1-HA and pLenti6 W118-mCherry expression plasmids at a 10:1 molar ratio in 1 mg/mL PEI in OptiMEM with untransfected cells as controls. Twenty-four hours post-transfection, cells were challenged with SVV-GFP at MOI=0.5 vp/cell for 16 h and imaged as described below. Parallel samples of transfected cells were harvested and analyzed via Western blot.

SVV-GFP Infections

Unless otherwise stated, cells were seeded in a tissue culture treated well plate (Corning) 24 h prior to infection. Plates were infected with SVV-GFP at an MOI=5.0 vp/cell and incubated at 37° C. for 8 or 16 h. NucBlue Live ReadyProbe reagent (Invitrogen) was added to each well and incubated at 37° C. for 20 min. Images of cells were obtained using an EVOS FL Auto fluorescence microscope (Invitrogen). For mixed culture in vitro experiments, parental H446 and H446 ANTXR1 KO mCherry cells were seeded as pure culture or seeded as a mixed culture with a 1:1 ratio. Cells were then challenged with SVV-GFP (MOI=0.1 vp/cell) for 16 h at 37° C. and subsequently imaged. For IFN response activity assays, DMS79 and H1618 cells were treated with media alone, media supplemented with 4 µM of histone deacetylase (HDAC) inhibitor MS-275 (Selleck) or Vorinostat (SAHA; LC labs), 25 Units/mL IFN-α (Thermo) or IFN-3 (R&D Systems), or 25 U/mL IFN-α/β and corresponding 5 µg/mL IFN-α (Thermo) or IFN-3 antibody (R&D Systems) for 24 h at 37° C. H446, H82, and H1618 cells were treated with media alone or media supplemented with 25 U/mL IFN-β for 24 h at 37° C. Cells were then challenged with SVV-GFP (H1618: MOI=0.5 vp/cell; DMS79, H446, H82: MOT-0.1 vp/cell) for 16 h at 37° C. and subsequently analyzed by flow cytometry. For blocking experiments, SVV-GFP (MOI=5) was incubated with 5 µg/mL ANTXR1-Fc or ANTXR2-Fc chimera, IgG-Fc (Sino Biological), or control (R&D Systems) on ice for 1 h and subsequently added to cells for 16 h at 37° C.

SVV-Cy5 Binding Experiment

SVV was incubated with the amine-reactive Cy5 dye (GE Healthcare) in sodium carbonate buffer (pH 9.3) for 1 h at room temperature (RT). Excess dye was removed by filtration through gel filtration columns (GE Healthcare) in HEPES buffer. Virus aliquots were stored at −80° C. parental, ANTXR1 KO, and TEX2 KO H446 cells were incubated with SVV-Cy5 for 30 min at 37° C. in OptiMEM. The non-permissive SCLC cell line, DMS114, was used as a negative control. Cells were then washed with FACS buffer three times before staining with LIVE/DEAD Fixable Aqua Dead Cell Stain Kit and fixed as described above. Samples were run on a BD LSR II Flow Cytometer (Becton Dickinson) using unstained cells and cells incubated with OptiMEM alone as controls. All compensation and gating were performed with FlowJo analysis software (TreeStar) as described below.

Co-Immunoprecipitations (Co-IP)

Magnetic Protein G Dynabeads (Invitrogen) were used for all immunoprecipitation experiments. Unless otherwise stated, Dynabeads and Dynabead-protein complexes were washed three times with PBS, pH 7.4 supplemented with 0.02% Tween-20 (Sigma Aldrich). Dynabeads were immobilized for manipulation and washing using a DynaMag magnet (Life Technologics). Proteins were eluted by boiling Dynabead-protein complexes for 10 min at 90° C. using RIPA buffer supplemented with NuPAGE sample reducing agent and LDS sample buffer. For initial ANTXR1-Fc and ANTXR2-Fc co-IP experiments, serial dilutions of Fc chimera proteins (0.25 µg) in PBS, pH 7.4 were incubated with 1 µL of 30 mg/mL Dynabeads for 10 min at room temperature. Dynabead-Fc complexes were washed and subsequently incubated with SVV ($2.0 \times 10^{10}$ vp) for 2 h at 4° C. Triplicate washes were repeated and dynabead-protein complexes were then subjected to protein elution. For co-IP using high stringency washes, PBS, pH 7.4 supplemented with 0.02% Tween-20 and increasing amounts of NaCl from 125 mM to 2 M were used to wash the Dynabead-protein complexes after SVV addition.

Western Blotting

Eluted Dynabead proteins or protein extracts were resolved on a 4-12% Bis-Tris polyacrylamide gel with MOPS running buffer (Life Technologies) and transferred to a polyvinylidene difluoride (PVDF) membrane (Millipore). For co-IP experiments, membranes were blotted with rabbit antisera against SVV (Neotropix) For ANTXR1 transfection cell lysates, membranes were blotted with commercial primary antibodies against the HA tag (Cell Signaling cat. No. 3724S) or glyceraldehyde phosphate dehydrogenase (GAPDH; Santa Cruz cat. no. sc-25778) or vinculin (Cell Signaling cat. No. 13901S) as loading controls. Immunoblotting was performed using horseradish peroxidase-conjugated secondary antibodies (Cell Signaling) and detection by chemiluminescence (GE Life Sciences).

Flow Cytometry Analysis

Parental and ANTXR1 KO cell lines were seeded in tissue culture treated 6-well plates 24 h prior to SVV-GFP infection. Cells were infected with SVV-GFP at the $TCID_{50}$ for each cell line and incubated at 37° C. for 6-16 h with uninfected cells as controls. Cells were subsequently harvested using Accutase enzyme cell detachment media (Gibco), pelleted by centrifugation, and washed with sterile PBS, pH 7.4 supplemented with 2% FCS and 0.5 mM EDTA (FACS buffer). Cells were stained with LIVE/DEAD Fixable Aqua Dead Cell Stain Kit (Invitrogen) for 30 min at 4° C., washed with FACS buffer, then fixed in 4% paraformaldehyde solution for 10 min at 4° C. For tumor samples, tumors were manually processed into single cell suspensions and subjected to ACK lysis buffer (Crystalgen) incubation to remove contaminating murine red blood cells. Cells were then stained with LIVE/DEAD Fixable Aqua Dead Cell Stain Kit and washed multiple times with FACS buffer. After a final wash with FACS buffer, cells were run on a BD LSR II Flow Cytometer (Becton Dickinson) using unstained cells and cells incubated with media alone as controls. For tumor samples, untreated pure parental and ANTXR1 KO mCherry tumors were processed and used as controls. All experimental samples were collected and performed in triplicate. Data from tumor samples represents average of 4-5 individual tumors. Additional gating and analysis was performed with FlowJo analysis software (TreeStar). Analyzed data and standard deviations were plotted using GraphPad Prism 6 software. Unpaired two-sided t tests were performed where applicable to determine statistical significance. Asterisks represent significance levels as follows: * $p \leq 0.05$,  $p \leq 0.01$, * $p \leq 0.001$, and **** $p \leq 0.0001$.

Gene Expression Analysis

Normalized gene expression data for cancer cell lines was downloaded from the Cancer Cell Line Encyclopedia (CCLE) or from the Pediatric Preclinical Testing Program (PPTP) (Barretina, J., et al. The Cancer Cell Line Encyclopedia enables predictive modelling of anticancer drug sensitivity. Nature 483, 603-607 (2012); Neale, G., et al. Molecular characterization of the pediatric preclinical testing panel. Clinical cancer research: an official journal of the American Association for Cancer Research 14, 4572-4583 (2008)). Custom content descriptor files (CDF) were used for both gene expression data sets. For CCLE microarray data, we used a CDF corresponding to ENTREZG—v15. For PPTP microarray data, which includes admixed mRNA of both human and mouse origin, we used a human specific H-spec CDF (Isella, C., et al. Stromal contribution to the colorectal cancer transcriptome. Nature genetics 47, 312-319 (2015)). To determine the appropriate cutoff for cell lines expressing ANTXR1, local modes in the density distribution of ANTXR1 expression were identified, the lowest of which was designated as non-expressed. The standard deviation of this peak was then determined and an expression cutoff equal to 10 standard deviations above the mode was set, based on the work of Zilliox et al (Zilliox, M. J. & Irizarry, R. A. A gene expression bar code for microarray data. Nature methods 4, 911-913 (2007)). Similar results were obtained using a Gaussian mixture model. Gene expression analysis was performed using the R statistical programming environment and the Bioconductor suite of tools. Differentially expressed genes were identified using LIMMA to fit a linear model to each gene and generate moderated t-statistics using an empirical Bayes approach. Gene set enrichment analysis was performed using CAMERA, a purely competitive gene set testing approach (Wu, D. & Smyth, G. K. Camera: a competitive gene set test accounting for inter-gene correlation. Nucleic Acids Res 40, e133 (2012)). Sample-wise enrichment was determined using GSVA (Hanzelmann, S., Castelo, R. & Guinney, J. GSVA: gene set variation analysis for microarray and RNA-seq data. BMC bioinformatics 14, 7 (2013)).

Cryo-Electron Microscopy

Equal volumes of virions at 0.2 mg/ml and ANTXR1 at 1 mg/ml were mixed, giving a ratio of ~10:1 receptors per binding site. The samples were mixed and kept for 90 min at 37° C. and transferred on ice for another 90 min. Specimens were prepared by applying 3 µL of purified virus on glow discharged Quantifoil holey carbon grids (Quantifoil Micro Tools GmbH, Grossloebichau/Jena, Germany). The excess buffer was blotted and the grid was flash plunged into liquid ethane using a Leica KF80 cryo fixation device (C. Reichert Optische Werke AG, Vienna, Austria). Grids were loaded onto a Gatan 914 Cryoholder (Pleasanton, Calif., USA). Images were collected on a JEOL JEM2200FS microscope (JEOL Ltd, Tokyo, Japan) operated at 200 kV using minimal dose conditions with an electron dose of ~30 electrons/Å$^2$. An in-column omega energy filter was used to improve image contrast by zero-loss filtering with a slit width of 25 eV. Automated data collection was carried out using SerialEM software. The micrographs were recorded at a defocus between 1 and 3 µm, on a 4×4 k CMOS camera (TVIPS; Gauting, Germany) at a calibrated magnification of 50,000 corresponding to a pixel size of 3.12 Å.

A number of 17400 individual virus particles were selected from micrographs using the E2BOXER software (Tang, G., et al. EMAN2: an extensible image processing suite for electron microscopy. Journal of structural biology 157, 38-46 (2007)). Contrast Transfer Function parameters were calculated using CTFFIND3 (Mindell, J. A. & Grigorief, N. Accurate determination of local defocus and specimen tilt in electron microscopy. Journal of structural biology 142, 334-347 (2003)), and micrographs with poor CTF estimates were discarded. Orientation, classification and refinement were done in Relion (Scheres, S. H. RELION: implementation of a Bayesian approach to cryo-EM structure determination. Journal of structural biology 180, 519-530 (2012)) using as initial reference a strongly low pass version of the SVV atomic model (Venkataraman, S., et al. Structure of Seneca Valley Virus-001: an oncolytic picornavirus representing a new genus. Structure 16, 1555-1561 (2008)). By calculating the Fourier shell correlation between two halves of the data set, the resolution of the map was estimated to be 14.5 Å. The reconstructed map was visualized using Chimera (Pettersen, E. F., et al. UCSF Chimera—a visualization system for exploratory research and analysis. Journal of computational chemistry 25, 1605-1612 (2004)).

Example 2: Genome-Wide Loss-of-Function Screens Identify ANTXR1 as Essential for SVV Infection The pooled GeCKO v2 human sgRNA library targets over 19,000 genes within the human genome and has the ability to efficiently knock out genes using the Cas9 DNA nuclease (Shalem, O., et al. Genome-scale CRISPR-Cas9 knockout screening in human cells. Science 343, 84-87 (2014); Sanjana, N. E., Shalem, O. & Zhang, F., Improved vectors and genome-wide libraries for CRISPR screening. Nature methods 11, 783-784 (2014); Cong, L., et al. Multiplex genome engineering using CRISPR/Cas systems. Science 339, 819-823 (2013); Mali, P., et al. RNA-guided human genome engineering via Cas9. Science 339, 823-826 (2013); Jinek, M., et al. A programmable dual-RNA-guided DNA endonuclease in adaptive bacterial immunity. Science 337, 816-821 (2012)). Due to the high efficiency of gene disruption in haploid cells, we performed a GeCKO screen in one of the only known human haploid cell lines, the chronic myelogenous leukemia (CML) cell line HAP1, which we found to be permissive to SVV at relatively high MOI (Carette, J. E., et al. Ebola virus entry requires the cholesterol transporter Niemann-Pick C1. Nature 477, 340-343 (2011)). HAP1-Cas9 cells were transduced by the pooled GeCKO library lentivirus and challenged with an SVV infection at a high MOI to select for resistant cells (FIG. 1, panel a). Genomic DNA was extracted from the expanded surviving cell population and subsequently analyzed by high-throughput sequencing to determine changes in sgRNA representation compared to controls. Representation of non-targeting control sgRNAs was maintained from the plasmid pools until the end of the screen; however, notable changes were observed in targeting sgRNAs, reflecting loss of sgRNAs that target essential genes. The most significantly enriched sgRNAs in the SVV selected pool were found to target the ANTXR1 gene, which encodes the anthrax toxin receptor 1 (Bradley, K. A., Mogridge, J., Mourez, M., Collier, R. J. & Young, J. A. Identification of the cellular receptor for anthrax toxin. Nature 414, 225-229 (2001)). ANTXR1 and the testis expressed 2 gene, TEX2 were the only genes with multiple sgRNAs significantly enriched in the SVV resistant sample (FIG. 1, panel b). Highly enriched sgRNAs were individually tested for the ability to confer resistance to SVV to HAP1 cells (FIG. 1, panel c). 6 sgRNAs were observed targeting 3 different genes that conferred SVV resistance after gene knockout in HAP 1 cells, including three separate sgRNAs targeting the ANTXR1 gene. Both enriched sgRNAs targeting the TEX2 gene conferred resistance as well as 1 sgRNA targeting the NR2C2 gene.

To confirm the results in a cell line of immediate relevance to neuroendocrine cancers, the GeCKO screen was repeated in the highly SVV-permissive H446 SCLC cell line. GeCKO lentivirus transduced H446-Cas9 cells were challenged with SVV at an MOI of 1 vp/cell. The percentage of surviving cells after SVV infection was much lower than in the HAP1 screen, allowing isolation of individual cell colonies, instead of a pooled population. Genomic DNA from each colony was extracted and individual sgRNAs were identified by Sanger sequencing (FIG. 1, panel d). In 23 of 25 resistant colonies (92%) sgRNAs targeting ANTXR1 were present, and comprised three independent sgRNAs targeting ANTXR1. Each sgRNA identified in the H446 screen was tested individually in a secondary screen of parental H446 cells for the ability to confer SVV resistance (FIG. 1, panel e). All three ANTXR1-targeting sgRNAs identified in the screen were able to confer resistance to SVV; however, no other candidate sgRNAs altered SVV permissivity in parental H446 cells.

Figure 2:
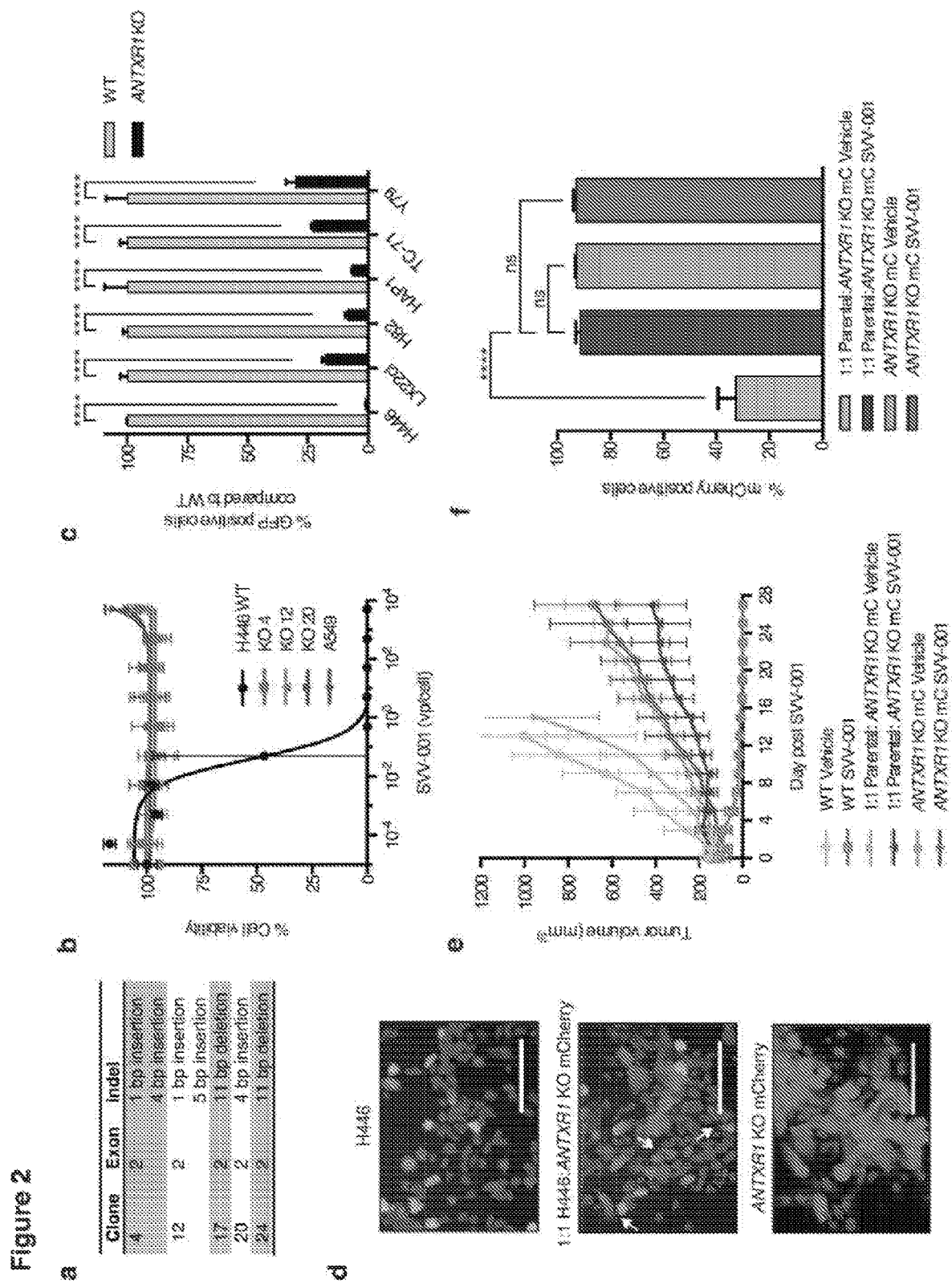
FIG. 2 shows knockout of ANTXR1 leads to the loss of SVV permissivity. Panel a) Summary table of ANTXR1 indels in five selected H446 ANTXR1 KO colonies from the GeCKO screen. Panel b) Three of the H446 ANTXR1 KO cell lines were challenged with increasing MOIs of SVV for 72 h. Cell viability was determined via AlamarBlue. Parental H446 cells and the non-permissive NSCLC cell line A549 were used as positive and negative controls, respectively. Each data point represents the average of 6 replicates with error bars representing standard deviation. Panel c) Permissive SCLC and pediatric cell lines were transduced with a sgRNA targeting ANTXR1. Parental (light grey) and ANTXR1 KO (black) cells were challenged with SVV-GFP and analyzed by flow cytometry. Each bar represents the average of 3 replicates with error bars representing standard deviation. Panel d) Parental H446 cells (top), H446 ANTXR1 KO mCherry cells (bottom), or 1:1 mixture of parental:ANTXR1 KO mCherry cells (middle) were challenged with SVV-GFP. White arrows indicate adjacent SVV-GFP infected parental H446 and uninfected ANTXR1 KO mCherry cells. Scale bars represent 100 μm Panel e) Parental H446 tumors (light green/dark green), H446 ANTXR1 KO mCherry tumors (pink/red), and 1:1 mixture of parental:ANTXR1 KO mCherry tumors (light purple/dark purple) were challenged with WT SVV-001 or PBS Vehicle. Tumor volumes were measured every other day. Each data point corresponds to average of 4-5 tumors with error bars representing standard deviation. Panel f) Tumors were excised at the experiment endpoint and analyzed by flow cytometry. Each bar represents the average of 4-5 tumors with error bars representing standard deviation.

Example 3: ANTXR1 is Necessary for Permissively in Neuroendocrine Cancer Cell Lines The genomic sequence of ANTXR1 was assessed in clones isolated from the H446 screen and found that all 5 ANTXR1 KO clones contained insertions or deletions (indels) in exon 2 of the ANTXR1 gene. These indels would lead to a frame shift mutation and premature stop codon, predicted to result in a truncated ANTXR1 protein (FIG. 2, panel a). The loss of SVV permissivity of the ANTXR1 KO clones was confirmed using a cell viability assay with parental H446 cells and non-permissive A549 cells as positive and negative controls, respectively (FIG. 2, panel b). After a 72 h incubation period with SVV, a significant loss of viability was observed with increasing MOI of SVV in parental H446 cells. Indicative of highly SVV resistant cells, all ANTXR1 KO lines as well as A549 cells showed no significant change in cell viability with MOI of SVV over 5 logs higher than effective exposures for parental H446 cells.

To determine whether ANTXR1 is essential for SVV infection in additional neuroendocrine cancer cell lines, we generated ANTXR1 KO lines in the SCLC cell lines H446, LX22cl, and H82, as well as HAP1 and the SVV-permissive pediatric cancer cell lines Y79 and TC-71. Each ANTXR1 KO line was challenged with an infectious SVV reporter virus that expresses GFP within the viral polyprotein (SVV-GFP) (Poirier, J. T., et al. Selective tropism of Seneca Valley virus for variant subtype small cell lung cancer. J Natl Cancer Inst 105, 1059-1065 (2013); Poirier, J. T., et al. Characterization of a full-length infectious cDNA clone and a GFP reporter derivative of the oncolytic picornavirus SVV-001. J Gen Virol 93, 2606-2613 (2012)). Cells were analyzed by flow cytometry using the corresponding parental cell line as a positive control (FIG. 2, panel c). As a negative control, we created an H446 cell line stably expressing an sgRNA targeting EGFP, to confirm loss of permissivity was due to the targeting ANTXR1 sgRNAs and not off-target effects. In all cases ANTXR1 KO profoundly decreased SVV-GFP infection?70% in the KO cell lines compared to the corresponding parental lines. ANTXR1 gene knockout leads to a loss of SVV permissivity in permissive cell lines of multiple tumor types.

Bystander cells lacking ANTXR1 expression were further examined to if they could be infected by neighboring cells through cell-cell spread in a mixed cell population containing both parental and ANTXR1 KO cells. First, an H446 ANTXR1 KO clone was created that stably expressed the mCherry fluorescent protein (ANTXR1 KO mCherry). Then, parental H446 and ANTXR1 KO mCherry cells were co-cultured at a 1:1 cell number ratio and the cells were challenged with SVV-GFP using pure parental and ANTXR1 KO mCherry cultures as controls (FIG. 2, panel d). As expected, only single GFP positive (GFP+) or mCherry positive (mCherry+) cells were observed but did not identify GFP+/mCherry+ cells in the admixed cell culture. Additionally, the above experiment was repeated in vivo with WT SVV-001 by engrafting immunodeficient nude mice with parental H446 cells, ANTXR1 KO mCherry cells, or a 1:1 mixture of parental and ANTXR1 KO mCherry cells (FIG. 2, panel e). Parental H446 tumors showed complete regressions upon administration of SVV-001 whereas the 1:1 parental:ANTXR1 KO mCherry tumor cohort showed only an initial delay in tumor progression. Furthermore, the resulting tumors that eventually progressed in the 1:1 parental:ANTXR1 KO mCherry SVV-001 cohort were significantly enriched in mCherry+ cells, indicating a loss of parental H446 cells (FIG. 2, panel f). As expected, ANTXR1 KO mCherry tumors were unaffected by the administration of SVV-001 compared to control.

Example 4: Defects in Innate Immune Signaling are Required for SVV Replication

Figure 3:
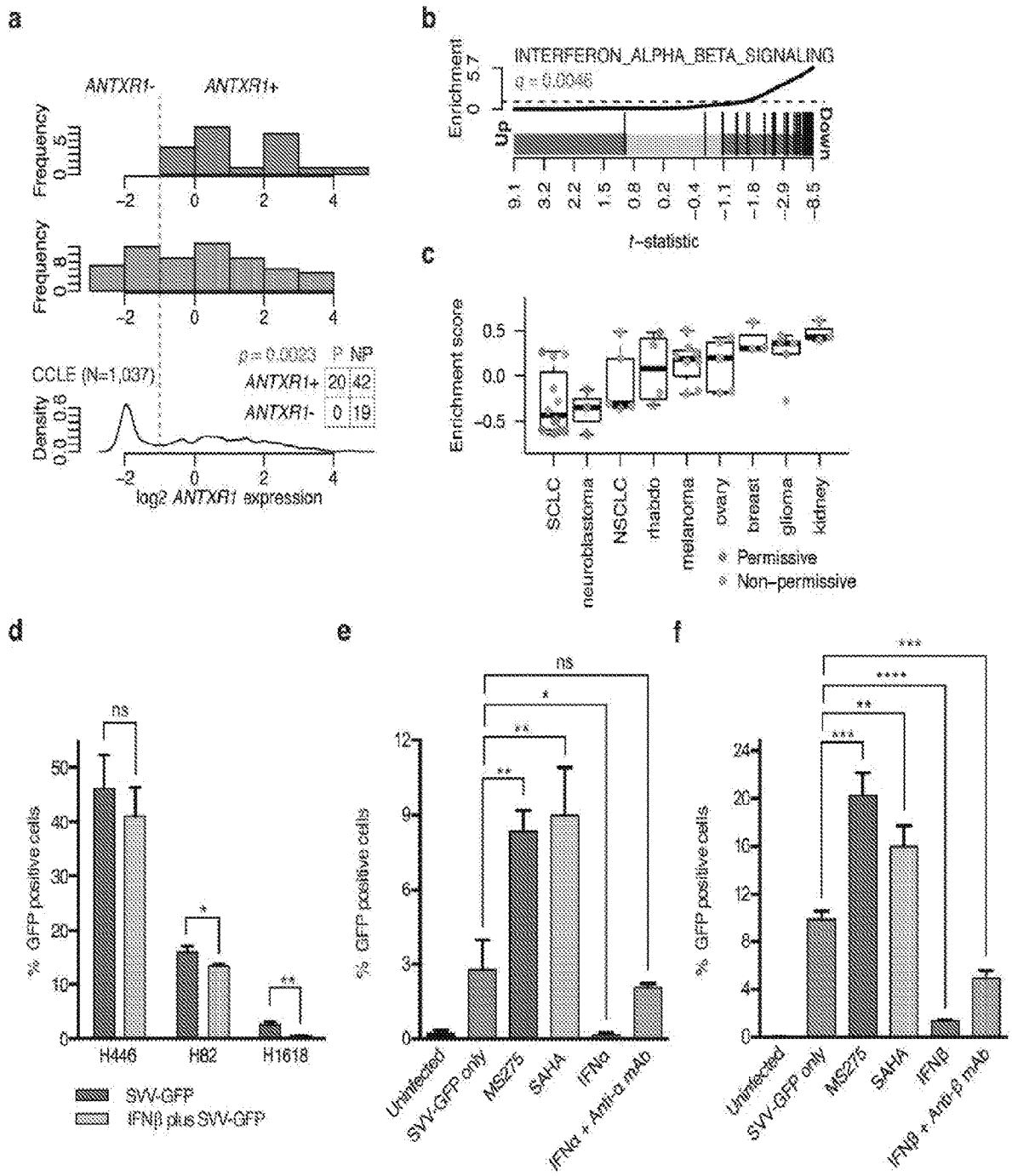
FIG. 3 shows ANTXR1 expression is significantly associated with permissivity. Panel a) Scaled log 2 ANTXR1 gene expression of permissive (top), non-permissive (middle) and all cell lines in the CCLE (bottom). ANTXR1 expression was significantly associated with permissivity (p=0.0023; Fisher's exact test). Panel b) An enrichment barcode plot depicting the negative enrichment of type I interferon signaling genes in permissive cell lines (q=0.0046). Panel c) Sample-wise enrichment scores were calculated for the top enriched gene set and plotted based on the histology of the tumor of origin. SCLC and neuroblastoma stand out as lacking genes involved in type I interferon signaling. Panel d) H446, H82, and H1618 cells (light blue) were pre-treated with IFNβ for 24 h prior to challenge with SVV-GFP and subsequent analysis by flow cytometry. Untreated cells (dark blue) were used as controls. Each bar in d-f represents the average of 3 replicates with error bars representing standard deviation. Panel e) H1618 and DMS79 Panel f) were pre-treated with HDAC inhibitors SAHA (light blue) or MS-275 (dark blue), IFNα/β (red), or IFNα/β with corresponding IFNα/β monoclonal antibodies (pink) for 24 h prior to challenge with SVV-GFP and subsequent analysis via flow cytometry. Uninfected (black) and untreated (green) cells were used as controls.

Whether ANTXR1 expression level in cell lines is predictive of permissivity was determined using publicly available gene expression data of the 1,037 cell lines in the Cancer Cell Line Encyclopedia (CCLE) (Barretina, J., et al. The Cancer Cell Line Encyclopedia enables predictive modelling of anticancer drug sensitivity. Nature 483, 603-607 (2012)). First, an expression cutoff was determined based on the distribution of expression in the CCLE (Zilliox, M. J. & Irizarry, R. A. A gene expression bar code for microarray data. Nature methods 4, 911-913 (2007)). Approximately 37% of cell lines fell below the expression cutoff (FIG. 3, panel a). Of the cell lines in the CCLE, 81 have been previously assessed for permissivity. Of these lines, biased toward inclusion of neuroendocrine cancer lines, 20 were found to be permissive. ANTXR1 expression was significantly associated with permissivity (p=0.0023, Fisher's exact test). Most strikingly, none of the 20 permissive cell lines lacked expression of ANTXR1, supporting the hypothesis that ANTXR1 is a required host factor for SVV infection.

While ANTXR1 expression appears to be a requirement for SVV permissivity, the CCLE dataset suggests that it is not sufficient: 42/62 (67.7%) of ANTXR1-expressing cell lines analyzed for permissivity were reported to be non-permissive. Meaningful gene expression differences between ANTXR1-expressing permissive and non-permissive classes were identified. Competitive gene set enrichment was used to identify significantly differentially expressed gene sets from the Reactome database (Milacic, M., et al. Annotating cancer variants and anti-cancer therapeutics in reactome. Cancers 4, 1180-1211 (2012); Croft, D., et al. The Reactome pathway knowledgebase. Nucleic Acids Res 42, D472-477 (2014)). 7 gene sets were identified, all of which were significantly down-regulated in permissive cell lines expressing ANTXR1. The most significant gene set was INTERFERON_ALPHA_BETA_SIGNALING, in which 34/44 (77%) of genes were significantly down-regulated in permissive cell lines. The enrichment for this gene set (q=0.0046) can be visualized in FIG. 3, panel b. A sample-wise analysis of gene expression was performed to see whether the gene set enrichment we observed was driven by cell lines derived from a particular tumor histology. Lack of expression of these gene sets was found enriched among SCLC and neuroblastoma cell lines (FIG. 3, panel c). To determine whether this expression signature was operant in vivo, a similar analysis of human tumor xenograft data from the Pediatric Preclinical Testing Program (PPTP) was performed and permissivity to SVV was found concordant with down-regulation of interferon signaling at baseline (Morton, C. L., et al. Initial testing of the replication competent Seneca Valley virus (NTX-010) by the pediatric preclinical testing program. Pediatric Blood Cancer 55, 295-303 (2010); Neale, G., et al. Molecular characterization of the pediatric preclinical testing panel. Clinical cancer research: an official journal of the American Association for Cancer Research 14, 4572-4583 (2008)). Taken together, these results suggest that robust permissivity to SVV requires both expression of the cellular receptor ANTXR1 and down-regulation of expression of antiviral IFN signaling genes at baseline.

IFN pathway activity within ANTXR1-expressing cell lines was assessed. It was hypothesized that highly SVV permissive cells have significantly down-regulated IFN response pathways and therefore may not respond to exogenous IFN pathway activation. The ability of exogenous IFNβ to decrease SVV permissivity in the highly permissive SCLC cell lines H446 and H82 was tested, as well as SVV refractory H1618 cells (FIG. 3, panel d). Relative permissivity of each cell line correlated strongly with the degree to which exogenous IFNβ could limit SVV infection. Previous studies have shown that permissivity to other oncolytic viruses could be increased due to indirect IFN pathway repression by pre-treating cells with histone deacetylase (HDAC) inhibitors, such as SAHA (vorinostat) or MS-275 (Nguyen, T. L., et al. Chemical targeting of the innate antiviral response by histone deacetylase inhibitors renders refractory cancers sensitive to viral oncolysis. Proc Natl Acad Sci USA 105, 14981-14986 (2008)). The ANTXR1-expressing non-permissive SCLC cell lines, H1618 and DMS79, were pre-treated with SAHA or MS-275 prior to challenging them with SVV-GFP and subsequent analysis by flow cytometry (FIG. 3, panel e-f). Compared to untreated cells, a significant increase in GFP+ cells was observed after HDAC treatment in both cell lines. Conversely, upon activation of the IFN pathways by pre-treatment with exogenous IFNα or IFNβ and subsequent SVV-GFP challenge, there was a decrease in SVV permissive, or GFP+ cells, for both cell lines. Additionally, the decrease in SVV permissive cells could be partially restored by pre-treating cells with IFNα/3 and a corresponding IFNα/1 monoclonal antibody that could block the IFN activity. These results confirm that SVV permissivity can be further dictated in ANTXR1-expressing cells by the expression of IFN response pathways. Additionally the activity of these pathways within the cell at the time of infection can alter SVV permissivity, but only in cells where the pathways are not significantly down-regulated.

Example 5: Re-Expression of ANTXR1 Rescues SVV Permissivity

Figure 4:
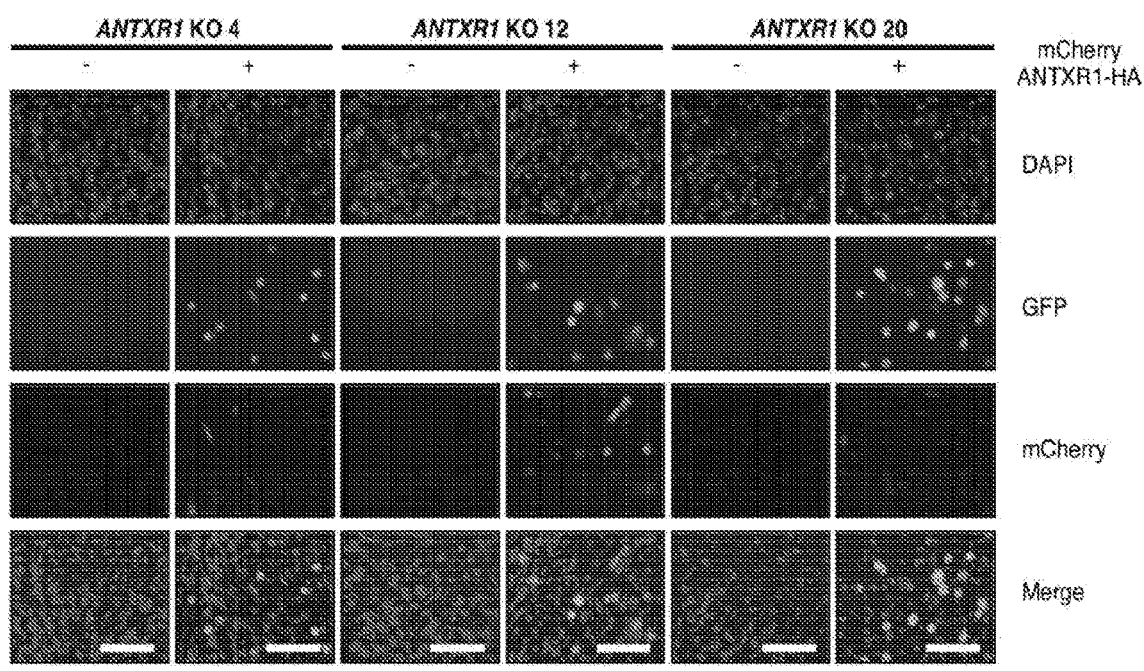
FIG. 4 shows re-expression of ANTXR1 reconstitutes SVV permissivity. Cells were co-transfected with the ANTXR1-HA and mCherry expression plasmids (A,D,F). Panel a) Three H446 ANTXR1 KO cell lines were transfected then challenged with SVV-GFP. Scale bar represents 100 μm. Panel b) H446 and LX22cl ANTXR1 KO cell lines were transfected, challenged with SVV-GFP, and analyzed by flow cytometry. mCherry transfected parental and ANTXR1 KO cells were used as positive and negative controls, respectively. Each bar represents the average of 3 replicates with error bars representing standard deviation. Panel c) H69 and H146 cells were transduced with a Dox-inducible ANTXR1-HA expression lentivirus. Parental and ANTXR1 expressing cells were incubated in absence or presence of 1 μg/mL doxycycline for 72 h, challenged with SVV-GFP, and analyzed by flow cytometry. Each bar represents the average of 3 replicates with error bars representing standard deviation.
Figure 4:
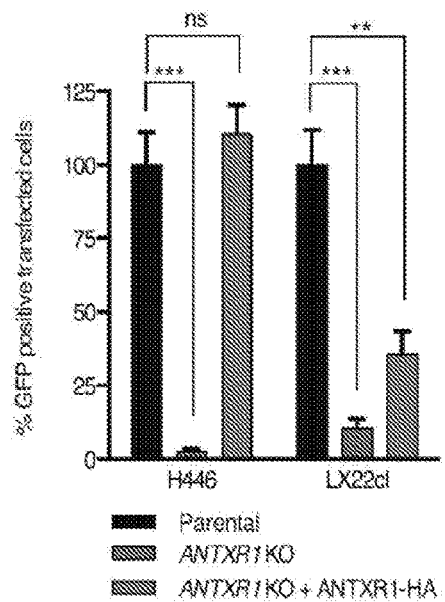
Figure 4:
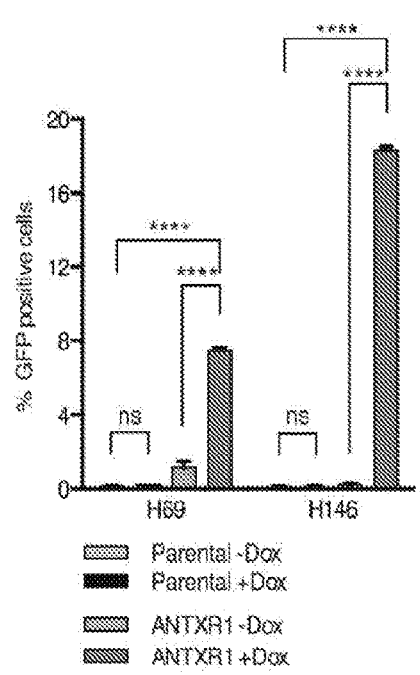

To confirm the specificity of the ANTXR1 sgRNAs, we evaluated whether exogenous re-expression of ANTXR1 could rescue permissivity to SVV in ANTXR1 KO cells. We co-transfected three H446 ANTXR1 KO lines with an ANTXR1-HA expression plasmid and an mCherry fluorescent protein expression plasmid and challenged the cells with SVV-GFP 16 h post transfection (FIG. 4, panel a). Compared to untransfected ANTXR1 KO cells that did not show any GFP+ cells, ANTXR1 KO cells transfected with the ANTXR1-HA expression plasmid consistently showed GFP+ cells, indicative of a productive SVV-GFP infection and rescue of SVV permissivity. To further test the importance of ANTXR1 expression in permissive cells, we co-transfected the H446 and LX22cl ANTXR1 KO lines with the ANTXR1-HA and mCherry expression plasmids, and subsequently incubated the cells with SVV-GFP. Cells were analyzed by flow cytometry and gated to select for transfected cells (mCherry+). Compared to parental mCherry+/GFP+ cells, we observed a significant decrease in the mCherry+/GFP+ population in ANTXR1 KO H446 and LX22cl cells that was rescued upon transfection with the ANTXR1-HA expression plasmid (FIG. 4, panel b). Expression of the ANTXR1-HA fusion protein was confirmed in each ANTXR1-HA transfected cell line by immunoblot using an HA tag specific antibody. Re-expression of ANTXR1 protein in ANTXR1 KO cell lines is sufficient to rescue SVV permissivity.

Example 6: Ectopic Expression of ANTXR1 is Sufficient to Induce SVV Permissivity Whether expression of ANTXR1 protein was sufficient to increase the permissivity of the non-permissive SCLC cell lines H69 and H146, which do not express the gene, was determined. After transduction with a doxycycline inducible ANTXR1-HA expression lentivirus, we incubated parental and ANTXR1 expressing H69 and H146 cells in the presence or absence of 1 μg/mL doxycycline for 72 h, challenged with SVV-GFP, and analyzed by flow cytometry (FIG. 4, panel c). Parental H69 and H146 cells and ANTXR1-transduced cells, in the absence of doxycycline, showed GFP+ populations under 1.5%, as expected. Upon doxycycline treatment, both ANTXR1-transduced H69 and H146 cells showed a significant increase in SVV-GFP infected cells to 7.46±0.17% and 18.3±0.20%, respectively. Expression of the ANTXR1-HA protein in the doxycycline induced cells was confirmed by Western blot. These data confirm that expression of the ANTXR1 protein is sufficient to induce permissivity in SVV-resistant SCLC cell lines.

Example 7: ANTXR1 Interacts Directly with SVV

As ANTXR1 is a transmembrane protein and required for SVV infection in various permissive SCLC cell lines, it was determined whether ANTXR1 interacts directly with SVV. An ANTXR1-Fc chimera or a control isotype IgG1 Fc protein was utilized for co-immunoprecipitation studies.

Figure 5:
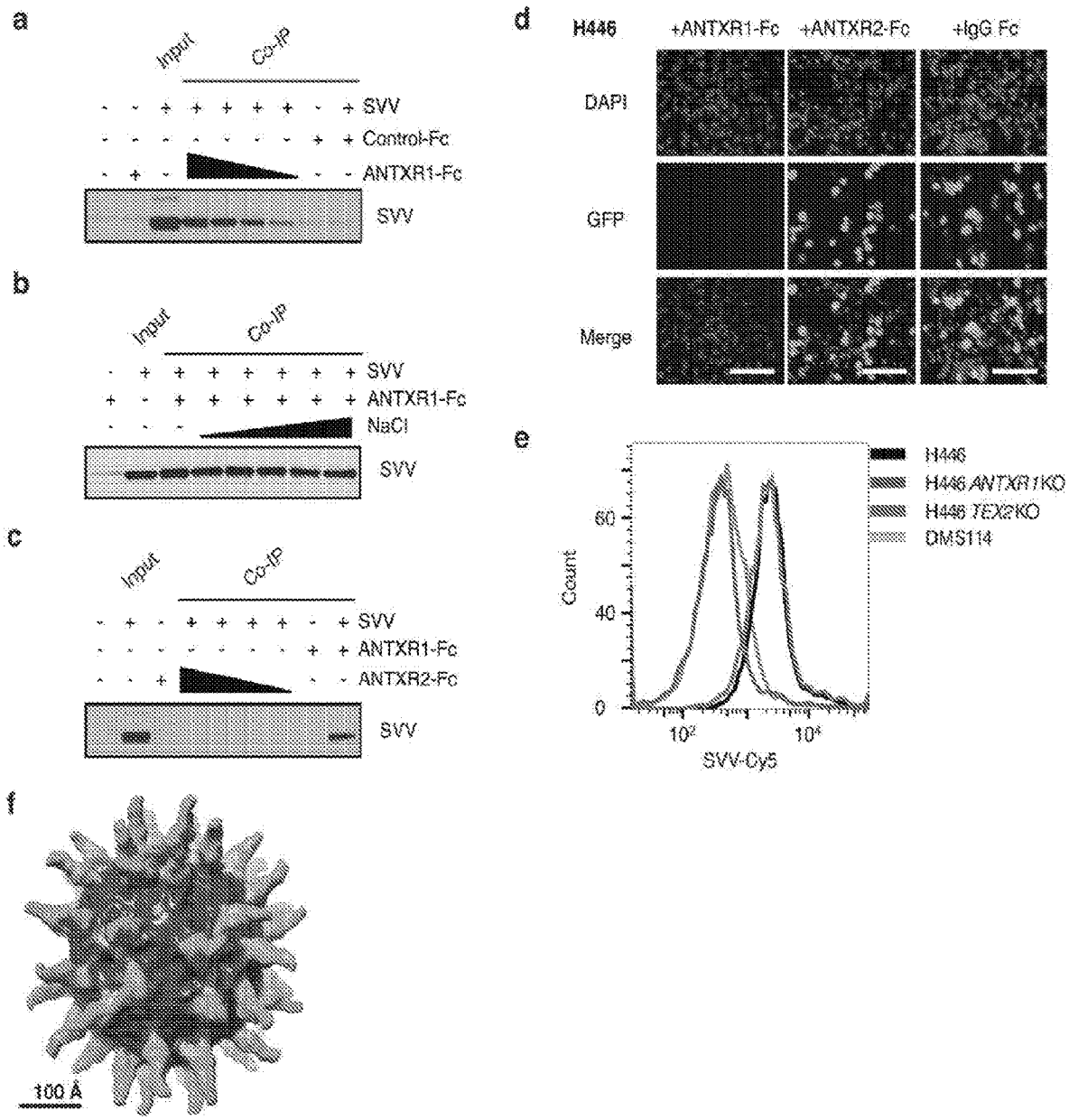
FIG. 5 shows SVV interacts directly with ANTXR1. Panel a) SVV was co-immunoprecipitated with decreasing amounts of an ANTXR1-Fc chimera. Bound proteins were eluted and analyzed by Western blot using an anti-SVV antibody. Input SVV was immunoblotted as a positive control. Panel b) SVV was co-immunoprecipitated with the ANTXR1-Fc chimera. Washes were performed with increasing concentrations of NaCl up to 2 M. Bound proteins were eluted and analyzed as described in A. Panel c) SVV was co-immunoprecipitated with the ANTXR1-Fc chimera or decreasing amounts of ANTXR2-Fc chimera and analyzed as described in A. Panel d) SVV-GFP was pre-incubated with the ANTXR1-Fc chimera, ANTXR2-Fc chimera, or IgG-Fc isotype control prior to a 8 h incubation with parental H446 cells. Cell nuclei were stained with a NucBlue LiveReady probe. Scale bar represents 100 μm. Panel e) ANTXR1 KO (blue) and TEX2 KO (red) cells were incubated with SVV-Cy5 and analyzed by flow cytometry. Parental H446 (black) and DMS114 (grey) cells were used as positive and negative controls for SVV binding, respectively. Panel f) Cryo-EM density map of SVV capsid (blue) bound to ANTXR1-Fc chimera (green).

After incubating Fc-bead complexes with SVV, all bound proteins were eluted and analyzed by Western blot using SVV rabbit antisera (FIG. 5, panel a). In all serially diluted ANTXR1-Fc samples incubated with SVV, viral protein bands were observed as well as a decrease in intensity of the bands corresponding to a decrease of bound ANTXR1-Fc protein. Any SVV protein bands were not detected in samples incubated with the IgG1 Fc isotype control or samples not incubated with SVV. After confirming a direct interaction, the ANTXR1-Fc chimera co-immunoprecipitation studies were repeated in the presence of increasing amounts of sodium chloride (NaCl) to investigate the strength of the interaction in vitro under high ionic strength (FIG. 5, panel b). The intensity of viral protein bands did not change significantly with increasing salt concentration up to 2M NaCl. As ANTXR1 has high sequence similarity to the high-affinity anthrax receptor, ANTXR2, the co-immunoprecipitation was performed with the ANTXR2-Fc chimeric protein using the ANTXR1-Fc protein as a positive control (Bradley, K. A., Mogridge, J., Mourez, M., Collier, R. J. & Young, J. A. Identification of the cellular receptor for anthrax toxin. Nature 414, 225-229 (2001)). Any bands were not observed corresponding to viral proteins in ANTXR2-Fc samples incubated with SVV, indicating the absence of an interaction between the extracellular domain of ANTXR2 and SVV (FIG. 5, panel c). Bands corresponding to viral protein were observed only in ANTXR1-Fc samples. These results indicate that ANTXR1, and not ANTXR2, can directly interact with SVV in a high affinity and stable interaction.

Additionally it was investigated which region of the ANTXR1 extracellular domain was essential for the interaction with SVV and was therefore, essential for rescue of SVV permissivity in ANTXR1 KO cells. An N-terminal deletion series of ANTXR1-HA expression plasmids was created that deleted increasing regions of the extracellular domain sequence of the ANTXR1 protein while preserving the signal peptide sequence. The ability of the truncated expression plasmids to rescue SVV permissivity in one of the H446 ANTXR1 KO clones was then tested. Unlike full-length ANTXR1 protein, all ANTXR1 truncations were unable to rescue SVV permissivity when challenged with SVV-GFP. Full-length and truncated ANTXR1-HA protein expression was confirmed via Western blot. These results suggest there are required residues for the interaction of SVV and ANTXR1 located in the most N-terminal region of the ANTXR1 protein.

Example 8: Soluble ANTXR1-Fc Chimera Blocks SVV Infection In Vitro

It was determined if the interaction between the SVV and ANTXR1-Fc or ANTXR2-Fc chimera could attenuate a cellular SVV infection. SVV-GFP was incubated with the ANTXR1-Fc, ANTXR2-Fc, or IgG1-Fc protein prior to an overnight incubation with parental H446 cells and subsequent analysis by fluorescence microscopy (FIG. 5, panel d). Cells incubated with SVV-GFP and IgG1-Fc or ANTXR2-Fc protein showed high levels of GFP+ cells indicative of a productive SVV infection. Cells incubated with SVV-GFP and ANTXR1-Fc protein showed no detectable GFP+ cells, indicating a substantial lack of SVV-GFP infection in these cells. These results demonstrate that only exogenous ANTXR1 protein and not ANTXR2 protein is able to block a cellular SVV-GFP infection, and further support ANTXR1 as the primary cellular receptor for SVV.

Example 9: Loss of ANTXR1 Protein Expression Abrogates SVV Binding to Permissive Cells It was determined if ANTXR1 KO cells had lost the ability to bind SVV. It was also assessed the potential role of TEX2, another candidate from the HAP1 screen, in binding SVV. Parental, ANTXR1 KO, and TEX2 KO H446 cells were incubated with WT SVV labeled with the fluorophore Cy5 (SVV-Cy5) and the cells were analyzed by flow cytometry using the non-permissive SCLC cell line, DMS114, as a negative control for SVV binding (FIG. 5, panel e). Parental H446 incubated with SVV-Cy5 showed a high level of fluorescence (mean fluorescence (MF)=2,373) compared to DMS114 cells incubated with SVV-Cy5 (MF=425). TEX2 KO H446 cells showed a similar fluorescence profile to parental H446 cells (MF=2,233), indicating there was no loss of SVV binding ability corresponding to loss of TEX2 protein expression. In contrast, ANTXR1 KO H446 cells showed a markedly diminished fluorescence profile similar to the negative control line, DMS114 (MF=358). Loss of SVV binding was only observed in ANTXR1 KO cells, indicating that not only does ANTXR1 bind directly to SVV based on co-IP data, but that it is the major binding determinant for the virus in intact cells.

Example 10: Cryo-EM of Capsid-Receptor Complex

The complex of SVV was analyzed bound to the ANTXR1-Fc chimeric protein by cryo-electron microscopy. Picornaviruses have an icosahedral capsid formed by 60 copies of a protomer consisting of three major capsid proteins VP1, VP2 and VP3 and a fourth much smaller protein, VP4 positioned in the interior of the capsid. Copies of VP1 are assembled around the five-fold axis, while VP2 and VP3 alternate around the three-fold axis (Tuthill, T. J., Groppelli, E., Hogle, J. M. & Rowlands, D. J. Picornaviruses. Current topics in microbiology and immunology 343, 43-89 (2010)). The reconstruction matches the existing atomic model of the virus (Venkataraman, S., et al. Structure of Seneca Valley Virus-001: an oncolytic picornavirus representing a new genus. Structure 16, 1555-1561 (2008)) when filtered to 14.5 Å resolution (FIG. 5, panel f). Additionally, the map displays the receptor subdomains distributed radially around the five-fold axis, in crown-like geometry similar to other picornaviruses, such as poliovirus (Strauss, M., et al. Nectin-like interactions between poliovirus and its receptor trigger conformational changes associated with cell entry. Journal of virology 89, 4143-4157 (2015)), rhinovirus (Kolatkar, P. R., et al. Structural studies of two rhinovirus serotypes complexed with fragments of their cellular receptor. The EMBO journal 18, 6249-6259 (1999)) or coxackieviruses (Organtini, L. J., Makhov, A. M., Conway, J. F., Hafenstein, S. & Carson, S. D. Kinetic and structural analysis of coxsackievirus B3 receptor interactions and formation of the A-particle. Journal of virology 88, 5755-5765 (2014)). The map revealed the receptor binding quasi-perpendicular to the capsid close to the center of the protomer, making contact with all three major capsid proteins and centered around the 'puff' loop of VP2.

The foregoing descriptions of specific embodiments of the present application have been presented for purposes of illustration and description. They are not intended to be exhaustive or to limit the application and method of use to the precise forms disclosed. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that, while these words, and/or other words that can be synonymous to one another, can be used synonymously herein, that there can be instances when such words can be intended to not be used synonymously. Further, to the extent that the knowledge of one of ordinary skill in the art has not been explicitly incorporated by reference herein above, it can be explicitly incorporated herein in its entirety.

The invention claimed is:

1. A method for treating cancer in a subject, comprising:
   a) in a cancerous tissue from the subject, determining:
      an expression level of anthrax toxin receptor 1 (ANTXR1), and
      an expression level of a type I interferon (IFN-I); and
   b) administering, to the subject, a therapeutic agent in combination with an effective amount of Seneca Valley Virus (SVV) if:
      a normal expression level or an elevated expression level of ANTXR1 is detected in the cancerous tissue of the subject, and
      a decreased expression level of IFN-I is detected in the cancerous tissue of the subject.

2. The method of claim 1, wherein the decreased expression level of IFN-I is achieved by administering an IFN-I inhibitor comprising at least one of a histone deacetylase (HDAC) inhibitor or an IFN-I antibody.

3. The method of claim 2, wherein the HDAC inhibitor comprises MS-275 or vorinostat.

4. The method of claim 2, wherein the IFN-I antibody comprises an IFN-α monoclonal antibody or an IFN-β monoclonal antibody.

5. The method of claim 1, wherein the therapeutic agent comprises a checkpoint inhibitor.

6. The method of claim 5, wherein the checkpoint inhibitor comprises Nivolumab, Pembrolzumab, or Ipilimumab.

7. The method of claim 1, wherein the SVV is administered by a direct injection thereof into the cancerous tissue.

8. The method of claim 1, wherein the subject is a subject with at least one of small cell lung cancer, neuroblastoma, retinoblastoma, medulloblastoma, rhabdomyosarcoma or pediatric neuroendocrine solid tumor.

9. The method of claim 1, wherein the subject is a subject with small cell lung cancer.

10. The method of claim 1, wherein the expression level of ANTXR1 in the cancerous tissue is determined at a transcriptional level.

11. The method of claim 1, wherein the expression level of ANTXR1 in the cancerous tissue is determined at a translational level.

12. The method of claim 1, wherein the expression level of IFN-I in the cancerous tissue is determined at a transcriptional level.

13. The method of claim 1, wherein the expression level of IFN-I in the cancerous tissue is determined at a translational level.

14. The method of claim 1, wherein the IFN-I comprises an α-interferon or a β-interferon.

15. The method of claim 1, wherein the decreased expression level of IGN-I is acheived by administering an IFN-I inhibitor.

* * * * *